US008777892B2

(12) United States Patent
Sandford et al.

(10) Patent No.: US 8,777,892 B2
(45) Date of Patent: Jul. 15, 2014

(54) PORTABLE PERITONEAL DIALYSIS SYSTEM

(75) Inventors: Harold F. Sandford, Groton, MA (US); Norma J. Ofsthun, Lexington, MA (US); Amanda K. Stennett, Waltham, MA (US); Jiunn Yeong Teo, Pleasant View, UT (US); Cheryl Ford, Ogden, UT (US); Benjamin J. Lipps, Boston, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 425 days.

(21) Appl. No.: 12/610,969

(22) Filed: Nov. 2, 2009

(65) Prior Publication Data

US 2010/0114012 A1    May 6, 2010

Related U.S. Application Data

(60) Provisional application No. 61/198,102, filed on Nov. 3, 2008.

(51) Int. Cl.
*A61M 1/28* (2006.01)
*A61M 1/16* (2006.01)
*B01D 61/24* (2006.01)

(52) U.S. Cl.
CPC .............. *A61M 1/1696* (2013.01); *B01D 61/24* (2013.01); *A61M 1/28* (2013.01); *A61M 1/284* (2014.02); *A61M 2209/088* (2013.01); *B01D 61/243* (2013.01); *A61M 1/1694* (2013.01)
USPC .............. 604/29; 604/28; 210/645; 210/646; 210/647; 210/648

(58) Field of Classification Search
CPC ... A61M 1/1694; A61M 1/1696; A61M 1/28; A61M 1/284; A61M 2001/284; A61M 1/3472; A61M 1/14; A61M 1/34; A61M 1/3679; A61M 1/3687; A61M 5/165; A61M 2005/1655; B01D 61/24; B01D 61/243
USPC ......... 604/28, 29, 131, 4.01, 6.01, 6.09, 6.11; 210/264, 266, 645–648
See application file for complete search history.

(56) References Cited

U.S. PATENT DOCUMENTS 3,579,441 A    5/1971    Brown
3,825,493 A    9/1972    Brown et al.
(Continued)

FOREIGN PATENT DOCUMENTS

DE    31 10 128 A1    9/1982
EP    0003914 A2    9/1979
(Continued)

OTHER PUBLICATIONS

Blumenkrantz, M. J. et al., "Development of a Sorbent Peritoneal Dialysate Regeneration System—A Progress Report," *Dialysis Transplantation Nephrology*, pp. 213-219. (1978).

(Continued)

*Primary Examiner* — Quynh-Nhu H Vu
*Assistant Examiner* — Larry R Wilson
(74) *Attorney, Agent, or Firm* — Hamilton, Brook, Smith & Reynolds, P.C.

(57) ABSTRACT

A portable peritoneal dialysis system for a patient includes an inlet port for providing inflow to the patient's peritoneal cavity, an outlet port for providing outflow from the patient's peritoneal cavity, and a volume of dialysate for flow into and out of the patient's peritoneal cavity, thereby removing from the dialysate uremic waste metabolites that have diffused into the dialysate. The portable peritoneal dialysis system also includes a closed liquid flow loop, including a pump, for flowing the dialysate into and out of the patient's peritoneal cavity, and an organic- and phosphate-removing stage, including at least one replaceable cartridge in the closed liquid flow loop, the cartridge containing material for removing organic compounds and phosphate from dialysate removed from the patient's peritoneal cavity. The portable peritoneal dialysis system further includes a urea- and ammonia-removing stage, including at least one replaceable cartridge in the closed liquid flow loop, the cartridge containing material for removing urea and ammonia from dialysate removed from the patient's peritoneal cavity, the material being packed around semi-permeable hollow fibers with interior fiber walls that reject cations, thereby retaining cations in the dialysate.

25 Claims, 18 Drawing Sheets

(56) References Cited

U.S. PATENT DOCUMENTS

| | | | |
|---|---|---|---|
| 3,707,967 A | | 1/1973 | Kitrilakis et al. |
| 4,094,775 A | | 6/1978 | Mueller |
| 4,256,102 A | | 3/1981 | Monaco |
| 5,026,365 A | | 6/1991 | Rossini et al. |
| 5,284,470 A | | 2/1994 | Beltz |
| 5,350,357 A | * | 9/1994 | Kamen et al. ............ 604/29 |
| 5,409,903 A | | 4/1995 | Polak et al. |
| 5,549,674 A | | 8/1996 | Humes et al. |
| 5,902,336 A | | 5/1999 | Mishkin |
| 5,944,684 A | | 8/1999 | Roberts et al. |
| 6,022,477 A | * | 2/2000 | Luo et al. ............ 210/645 |
| 6,217,859 B1 | | 4/2001 | Chang et al. |
| 6,234,991 B1 | | 5/2001 | Gorsuch |
| 6,254,567 B1 | | 7/2001 | Treu et al. |
| 6,579,460 B1 | | 6/2003 | Willis et al. |
| 6,706,287 B2 | | 3/2004 | Ranganathan et al. |
| 6,719,907 B2 | | 4/2004 | Collins et al. |
| 6,960,179 B2 | | 11/2005 | Gura |
| 7,033,498 B2 | | 4/2006 | Wong |
| 7,208,092 B2 | | 4/2007 | Micheli |
| 7,276,042 B2 | | 10/2007 | Polaschegg et al. |
| 7,309,323 B2 | | 12/2007 | Gura et al. |
| 7,332,330 B2 | | 2/2008 | Humes et al. |
| 7,435,342 B2 | | 10/2008 | Tsukamoto |
| 7,597,677 B2 | | 10/2009 | Gura et al. |
| 7,867,214 B2 | | 1/2011 | Childers et al. |
| 7,988,854 B2 | | 8/2011 | Tsukamoto |
| 8,012,118 B2 | | 9/2011 | Curtin et al. |
| 2002/0052571 A1 | | 5/2002 | Fazio |
| 2002/0112609 A1 | | 8/2002 | Wong |
| 2002/0123715 A1 | | 9/2002 | Sorenson et al. |
| 2002/0187940 A1 | | 12/2002 | Masuda et al. |
| 2003/0105424 A1 | | 6/2003 | Karoor et al. |
| 2003/0114787 A1 | * | 6/2003 | Gura ............ 604/29 |
| 2004/0019312 A1 | | 1/2004 | Childers et al. |
| 2004/0082903 A1 | | 4/2004 | Micheli |
| 2004/0182787 A1 | | 9/2004 | Chevallet et al. |
| 2004/0254514 A1 | | 12/2004 | Gura |
| 2005/0123529 A1 | | 6/2005 | O'Loughlin et al. |
| 2005/0131332 A1 | | 6/2005 | Kelly et al. |
| 2006/0058731 A1 | | 3/2006 | Burnett et al. |
| 2007/0060786 A1 | * | 3/2007 | Gura et al. ............ 600/16 |
| 2007/0161113 A1 | | 7/2007 | Ash |
| 2007/0179431 A1 | | 8/2007 | Roberts et al. |
| 2007/0199898 A1 | | 8/2007 | Sakai et al. |
| 2007/0213665 A1 | | 9/2007 | Curtin et al. |
| 2008/0051696 A1 | * | 2/2008 | Curtin et al. ............ 604/29 |
| 2010/0314314 A1 | | 12/2010 | Ding et al. |

FOREIGN PATENT DOCUMENTS

| | | |
|---|---|---|
| EP | 0 064 393 A2 | 11/1982 |
| JP | 56051237 | 5/1981 |
| JP | 60-132644 | 7/1985 |
| WO | WO 84/00885 | 3/1984 |
| WO | WO 95/32736 A1 | 12/1995 |
| WO | WO 97/33474 | 9/1997 |
| WO | WO 98/00172 A2 | 1/1998 |
| WO | WO 98/16171 | 4/1998 |
| WO | WO 03/041764 A1 | 5/2003 |
| WO | WO 03/051422 A2 | 6/2003 |
| WO | WO 2004/009158 A2 | 1/2004 |
| WO | WO 2007/103411 A2 | 9/2007 |
| WO | WO 2009/083011 A2 | 7/2009 |

OTHER PUBLICATIONS

Blumenkrantz, M. J. et al., "Applications of the Redy® Sorbent System to Hemodialysis and Peritoneal Dialysis," *Artificial Organs*: 3(3): 230-236 (1979).

Gordon, A. et al., "Augmentation of Efficiency by Continuous Flow Sorbent Regeneration Peritoneal Dialysis," *Trans. Amer. Soc. Artif. Int. Organs*, 22: 599-603 (1976).

Raja, R. et al., "Recirculation Peritoneal Dialysis with Sorbent Redy Cartridge," *Nephron*, 16: 134-142 (1976).

Roberts, M. et al., "Regeneration of Peritoneal Dialysate (PD): A Step Towards a Continuous Wearable Artificial Kidney (CWAK)," *Journal of American Society of Nephrology*, 2(3): 367 (Sep. 1991).

Roberts, M. et al., "*Innovative* Peritoneal Dialysis: Flow-Thru and Dialysate Regeneration," *ASAIO Journal* 1999, 45: 372-378 (1999).

Ronco, Claudio, et al., "The Vicenza Wearable Artificial Kidney for Peritoneal Dialysis (ViWAK PD)," *Blood Purif* 25:383-388 (2007).

International Preliminary Report on Patentability and Written Opinion, International Application No. PCT/US2009/062967, mailing date May 12, 2011.

Notification of Transmittal of the International Search Report and the Written Opinion of the International Searching Authority, or the Declaration, from PCT/US2009/062967, mailed Jun. 25, 2010, 17 pages.

Notification Concerning Transmittal of International Preliminary Report on Patentability, from PCT/US2008/009891, mailed Mar. 4, 2010, 8 pages.

Notification of Transmittal of the International Search Report and the Written Opinion of the International Searching Authority for International Application No. PCT/US2010/047548; Date of Mailing: Dec. 6, 2010.

Baysal, S.H. and Uslan, A.H., "In Vitro Study of Urease/AlaDH Enzyme System Encapsulated into Human Erythrocytes and Research into its Medical Applications," *Art. Cells, Blood Subs., and Immob. Biotech.*, 30(1):71-77 (2002).

Chang, T.M.S., "Artificial Cells with Emphasis on Cell Encapsulation of Genetically Engineered Cells," *Artificial Organs*, 22(11):958-965 (1998).

Diaz-Buxo, J.A., "Continuous-Flow Peritoneal Dialysis: Update," *Advances in Peritoneal Dialysis*, 20:18-22 (2004).

Gordon, A., et al., "Sorbent Regeneration of Peritoneal Dialysate: An Approach to Ambulatory Dialysis," *Journal of Dialysis*, 1(2):145-164 (1976-1977).

Lewin, A., "Sorbent Based Regenerative Peritoneal Dialysis System," *Dialysis & Transplantation*, 7(8):831, 833 (1978).

O'Loughlin, J.A., et al., "Degradation of Low Molecular Weight Uremic Solutes by Oral Delivery of Encapsulated Enzymes," *ASAIO Journal*, 50:253-260 (2004).

O'Loughlin, J.A., et al., "In Vivo and in Vitro Degradation of Urea and Uric Acid by Encapsulated Genetically Modified Microorganisms," *Tissue Engineering*, 10(9110):1446-1455 (2004).

O'Loughlin, J.A., et al, "Oral Administration of Biochemically Active Microcapsules to Treat Uremia: New Insights into an Old Approach," *J. Biomater. Sci. Polymer Edn*, 15(11):1447-1461 (2004).

Prakash, S. and Chang, T.M.S., "Artificial Cells Containing Genetically Engineered *E. Coli* DH5 Cells for Urea and Ammonia Removal in Kidney and Liver Failure," *IEEE Engineering in Medicine and Biology 17th Annual Conference*, vol. 2:1729-1730 (1995).

Sparks, R.E., et al., "Removal of Waste Metabolites in Uremia by Microencapsulated Reactants," *Trans. Amer. Soc. Artif. Int. Organs*, XV:353-359 (1969).

Wolfe, E.A. and Chang, T.M.S., "Orally Ingested Microencapsulated Urease and an Adsorbent, Zirconium Phosphate, to Remove Urea in Kidney Failure," *The International Journal of Artificial Organs*, 10(4):269-274 (1987).

Chang, T.M.S., "A Comparison of Semipermeable Microcapsules and Standard Dialysers for Use in Separation," *Separation and Purification Methods*, 3(2): 245-262 (1974).

Chang, T.M.S., "Artificial Kidney, Artificial Liver, and Detoxifiers Based on Artificial Cells, Immobilized Proteins, and Immobilized Enzymes," In *Biomedical Applications of Immobilized Enzymes and Proteins*, T.M.S. Chang, eds. (NY: Plenum Press), pp. 281-295 (1977).

Chang, T.M.S., "Biodegradable Semipermeable Microcapsules Containing Enzymes, Hormones, Vaccines, and other Biologicals," *J. Bioengineering*, 1: 25-31 (1976).

Chang, T.M.S., "Encapsulation of Enzymes, Cell Contents, Cells, Vaccines, Antigens, Antiserum, Cofactors, Hormones and Proteins," in *Biomedical Applications of Immobilized Enzymes and Proteins*, T.M.S. Chang, eds. (NY: Plenum Press), pp. 69-90 (1977).

(56) References Cited

OTHER PUBLICATIONS

Chang, T.M.S., "Experimental Therapy Using Semipermeable Microcapsules Containing Enzymes and Other Biologically Active Material," in *Biomedical Applications of Immobilized Enzymes and Proteins*, T.M.S. Chang, eds. (NY: Plenum Press), pp. 147-162 (1977).

Chang, T.M.S., "Immobilization of Enzymes, Adsorbents, or Both within Semipermeable Microcapsules (Artificial Cells) for Clinical and Experimental Treatment of Metabolite-Related Disorders," *Birth Defects: Original Article Series, IX*(2): 66-76 (1973).

Chang, T.M.S., "Immobilized Enzymes and Their Biomedical Applications." In *Immobilized Enzymes, Antigens, Antibodies, and Peptides Preparation and Characterization*, H.H. Weetall, ed. (NY: Marcel Dekker, Inc.), pp. 245-292 (1975).

Notification of Transmittal of the International Search Report and the Written Opinion of the International Searching Authority for International Application No. PCT/US2008/009891, mailed on Dec. 15, 2008.

Notification Concerning Transmittal of International Preliminary Report on Patentability for International Application No. PCT/US2010/047548, mailed on Mar. 22, 2012.

Notification Concerning Transmittal of International Preliminary Report on Patentability for International Application No. PCT/US2008/009891, mailed on Mar. 4, 2010.

Colton, Clark K. "Analysis of Membrane Processes for Blood Purification," *Blood Purification*, 5:202-251, (1987).

Gura, V., et al., "Continuous Renal Replacement Therapy for Congestive Heart Failure: The Wearable Continuous Ultrafiltration System," *ASIO Journal*, pp. 59-61, (2006).

Gura, V., et al., "Continuous Renal Replacement Therapy for End-Stage Renal Disease," *Cardiovascular Disorder in Hemodialysis. Contrib. Nephrol. Basel, Karger*, 149:325-333, (2005).

Lanza, R.P., et al., "Devices Implanted as AV Shunts," *Pancreatic Islet Transplantation, III*:157-168, (1994).

Lysaght, M.J., et al., "Filtration Rates and Pressure Driving Force in AV Filtration," *Blood Purification*, 1:178-183, (1983).

Maki, T., et al., "Novel Delivery of Pancreatic Islet Cells to Treat Insulin-Dependent Diabetes Mellitus," *Clin. Pharmacokinet.*, 38(6):471-482, (1995).

Shaldon, S., et al., "Continuous Ambulatory Hemofiltration," *Trans. Am. Soc. Artif. Intern. Organs*, XXVI:210-212, (1980).

Non-Final Office Action dated Jun. 28, 2013, U.S. Appl. No. 12/873,875.

U.S. Non-Final Office Action dated Aug. 8, 2013 for U.S. Appl. No. 11/371,216.

Notice of Allowance dated Jan. 16, 2014 for U.S. Appl. No. 11/371,216.

Final Office Action dated Jan. 8, 2014 for U.S. Appl. No. 12/873,875.

\* cited by examiner

PORTABLE PERITONEAL DIALYSIS SYSTEM

RELATED APPLICATION

This application claims the benefit of U.S. Provisional Application No. 61/198,102, filed on Nov. 3, 2008.

The entire teachings of the above application are incorporated herein by reference.

BACKGROUND OF THE INVENTION

Renal dysfunction or failure and, in particular, end-stage renal disease, causes the body to lose the ability to remove water and minerals and excrete harmful metabolites, maintain acid-base balance, and control electrolyte and mineral concentrations within physiological ranges. Toxic uremic waste metabolites including urea, creatinine, uric acid, and phosphorus accumulate in the body's tissues, which can result in a person's death if the filtration function of the kidney is not replaced.

Dialysis is commonly used to replace kidney function by removing these waste toxins and excess water. In one type of dialysis treatment, hemodialysis, toxins are removed from a patient's blood externally in a hemodialysis machine. Blood passes from the patient through a dialyzer separated by a semi-permeable membrane from an externally-supplied dialysate. Waste and toxins dialyze out of the blood through the semi-permeable membrane into the dialysate, which is then discarded. Hemodialysis treatment typically lasts several hours and must be performed under medical supervision three or four times a week, requirements that significantly decrease a patient's autonomy and quality of life. Also, since hemodialysis is performed periodically instead of continuously, the patient's condition and general well-being tend to be poor both immediately before hemodialysis (when toxin levels are high) and after hemodialysis (when electrolytes are imbalanced), resulting in the patient having symptoms that range from nausea and vomiting to edema.

Peritoneal dialysis is another type of dialysis treatment used to replace kidney function in which sterile, pyrogen-free dialysis solution is infused into the patient's peritoneal cavity. The peritoneal membrane serves as a natural dialyzer and toxic uremic waste metabolites and various ions diffuse from the patient's bloodstream across the membrane into the dialysis solution due to their concentration gradients. At the same time, water is drawn into the peritoneal cavity by an osmotic gradient. The dialysis solution is removed, discarded and replaced with fresh dialysis solution on a semi-continuous or continuous basis. Draining, discarding and replacing the large volumes of solution needed for peritoneal dialysis is still inconvenient, unwieldy and expensive, especially for peritoneal dialysis treatment at home instead of at a treatment center.

To address this problem, devices have been designed that reconstitute used dialysate from hemodialysis and/or peritoneal dialysis solution as opposed to discarding it. The dialysate can be regenerated in a machine employing a device that eliminates urea from the solution. For example, the original REDY® (REcirculating DYalysis) Sorbent System (Blumenkrantz et al., *Artif. Organs* 3(3):230-236, 1978) consists of a sorbent cartridge having five layers through which dialysate solution containing uremic waste metabolites flows in order to be regenerated. The spent dialysate flows through a purification layer that removes heavy metals (e.g., copper and lead) and oxidants (e.g., chlorine and chloramine), an aluminum oxide layer containing urease bound to some of the aluminum oxide which degrades the urea in the dialysate into ammonia and carbon dioxide gas (in equilibrium with ammonium carbonate), a zirconium phosphate layer that adsorbs the ammonium ions produced from urea degradation along with other cations (e.g., sodium, potassium, magnesium and calcium), a hydrated zirconium oxide layer that binds phosphate and other anions (e.g., fluoride and sulfate) in exchange for acetate, and an activated carbon layer that adsorbs other organic compounds (e.g., creatinine and uric acid).

Typically, the sorbents used in devices such as the REDY® Sorbent System adsorb not only the urea degradation products, but also essential ions such as, for example, calcium and magnesium that have diffused into the dialysate. These ions must then be replaced in the patient. Typically, current sorbent-based hemodialysis machines replace these essential ions continuously using an extra pump and associated valve and control mechanisms, devices that increase the weight and complexity of a hemodialysis machine, and would present similar problems for a peritoneal dialysis system.

There is, therefore, a need for a dialysis device that is more convenient, safe and effective and that significantly improves a patient's quality of life over current devices and methods.

SUMMARY OF THE INVENTION

The present invention provides a portable peritoneal dialysis device that can be comfortably worn or carried by a patient and which can operate continuously or semi-continuously during periods of dialysis to clear uremic waste metabolites from a patient with renal dysfunction or failure, without overly depleting the patient's body of essential ions, such as, for example, calcium and magnesium.

A portable peritoneal dialysis system of this invention can include an inlet port for providing inflow to the patient's peritoneal cavity, an outlet port for providing outflow from the patient's peritoneal cavity, and a volume of dialysate for flow into and out of the patient's peritoneal cavity, thereby removing from the dialysate uremic waste metabolites that have diffused into the dialysate. This portable peritoneal dialysis system can also include a closed liquid flow loop, including a pump, for flowing the dialysate into and out of the patient's peritoneal cavity, and an organic- and phosphate-removing stage, including at least one replaceable cartridge in the closed liquid flow loop, the cartridge containing material for removing organic compounds and phosphate from dialysate removed from the patient's peritoneal cavity. In one embodiment, this material is packed around semi-permeable hollow fibers. This portable peritoneal dialysis system can further include a urea- and ammonia-removing stage, including at least one replaceable cartridge in the closed liquid flow loop, the cartridge containing material for removing urea and ammonia from dialysate removed from the patient's peritoneal cavity, the material being packed around semi-permeable hollow fibers with interior fiber walls that reject cations, thereby retaining cations in the dialysate. In another embodiment, the material in the cartridge for removing organic compounds and phosphate can include a mixture of activated carbon and zirconium oxide. In yet another embodiment, the material in the cartridge for removing urea and ammonia can include urease and strong acid cation exchange resin or sorbent, such as an ion exchange sorbent. In one embodiment, the urease can be in the form of cross-linked jack bean meal polyethylenimine-carbon composite. In another embodiment, the portable peritoneal dialysis system can further include an ammonia-removing stage, including at least one replaceable cartridge in the closed liquid flow loop, the cartridge containing material for removing ammonia from dialysate removed from the patient's peritoneal cavity, the material being packed around hollow fibers with interior fiber walls that reject cations, thereby retaining cations in the dialysate. In one embodiment, the semi-permeable hollow fibers with interior fiber walls that reject cations can reject calcium, magnesium, potassium, and sodium cations. In another embodiment, the material in the cartridge for removing ammonia can include strong acid cation exchange resin or sorbents, including ion exchange sorbents. In yet another embodiment, the portable peritoneal dialysis system can further include an organic- and phosphate-removing and pH-control stage, including at least one replaceable cartridge in the closed liquid flow loop, the cartridge containing material for removing organic compounds from dialysate removed from the patient's peritoneal cavity and material for controlling the pH of the dialysate at or near physiological pH. In one embodiment, the material in the cartridge for removing organic compounds can include activated carbon, and the material in the cartridge for controlling the pH of the dialysate can include a mixture of zirconium oxide and sodium zirconium carbonate.

In another embodiment, the portable peritoneal dialysis system can be configured as a belt adapted to be worn by the patient, wherein each cartridge of each stage is substantially rectangular and sufficiently small to be concealable under a patient's clothing. In another embodiment, the portable peritoneal dialysis system can be configured as an integrated loop adapted to be worn by a patient as a belt or docked into a tabletop docking unit. In yet another embodiment, the portable peritoneal dialysis system can be configured as a tabletop unit.

The invention is also directed to a method for providing peritoneal dialysis to a patient using a portable peritoneal dialysis system including a closed liquid flow loop for flowing a volume of dialysate into and out of the patient's peritoneal cavity and through dialysate regenerating stages. The method includes flowing a volume of dialysate from the patient's peritoneal cavity through an organic- and phosphate-removing stage, including at least one replaceable cartridge in the closed liquid flow loop, the cartridge containing material for removing organic compounds and phosphate from dialysate removed from the patient's peritoneal cavity. Thereafter, the method further includes flowing the volume of dialysate through semi-permeable hollow fibers contained in a urea- and ammonia-removing stage, including at least one replaceable cartridge in the closed liquid flow loop, the cartridge containing material for removing urea and ammonia from dialysate removed from the patient's peritoneal cavity, the material being packed around the semi-permeable hollow fibers, the semi-permeable hollow fibers having interior fiber walls that reject cations, thereby retaining cations in the dialysate while removing from the dialysate uremic waste metabolites that have diffused into the dialysate, to produce regenerated dialysate, and introducing the regenerated dialysate into the patient's peritoneal cavity.

Unlike dialysis systems to date, the portable peritoneal dialysis system of the invention provides for a dialysis device that can allow the patient to maintain a more normal, active lifestyle. Due to the regeneration of the peritoneal dialysis solution, a relatively small volume of dialysate needs to be circulated in the portable peritoneal dialysis system, which allows the system to be relatively small and lightweight and thus comfortable to wear or carry. As the portable peritoneal dialysis system is able to operate continuously or semi-continuously during periods of dialysis through regeneration of the dialysate, it improves a patient's overall well-being and quality of life, freeing the patient from dialysis systems that are labor-intensive, time-consuming and/or require medical supervision. Moreover, the portable peritoneal dialysis system regenerates the dialysate without removing certain essential ions from the dialysate and, ultimately, from the patient's body. This is most advantageous as, currently, equipment to replace these essential ions generally includes an extra pump that increases the weight and complexity of a portable peritoneal dialysis system.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
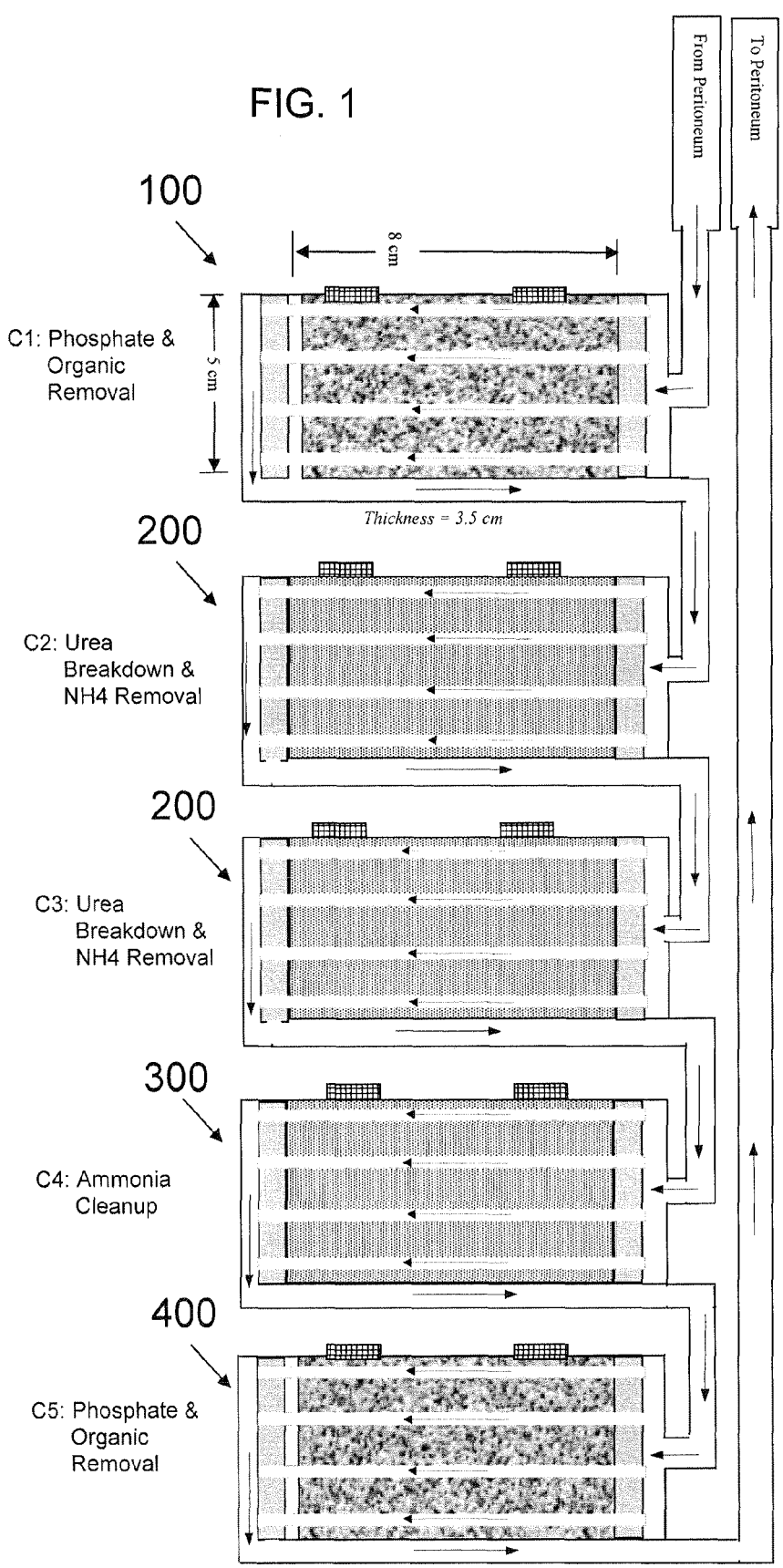
FIG. 1 is a schematic illustration of a portable peritoneal dialysis system according to this invention.

The present invention generally relates to a portable peritoneal dialysis system that removes uremic waste metabolites from a patient suffering from a disorder associated with the accumulation of uremic toxins (e.g., chronic kidney failure). The system can be used to treat a disorder such as, for example, renal disease, including early renal disease, renal dysfunction or renal failure (e.g., end stage renal disease). As used herein, the terms "uremic waste metabolites" and "uremic solutes" refer to compounds, such as those containing nitrogen, produced by the body as waste products and includes compounds like urea, uric acid, creatinine, phosphorus, and β-2-microglobulin, and other materials. See Vanholder R. et al., *Kidney International* 63:1934-1943, (2003). Renal failure or dysfunction leads to uremic toxicity, which occurs when the levels of uremic waste metabolites in a patient are elevated compared to the levels of the toxins in individuals with normal renal function.

Thus, the present invention relates to a portable peritoneal dialysis system that, unlike previous systems and devices, can be small enough in size to be wearable or portable without significant burden to a patient. The peritoneal dialysis can be performed continuously or semi-continuously, as the peritoneal dialysis system contains cleaning stages that each include one or more replaceable cartridges that regenerate the dialysate that is then circulated in the system. An example of desired amounts for daily removal of uremic solutes from a typical patient by a portable peritoneal dialysis (PD) system, while maintaining physiological pH of about 7.4 of the dialysate, are listed in Table 1. As indicated in Table 1, the maximum desired amounts are, for example, removal from a patient that has missed a treatment, or has a substantially larger muscle mass than a typical patient, or is particularly non-compliant with dietary restrictions.

TABLE 1

An Example of a Desired Daily Uremic Solute Removal Requirements for Portable PD System

| Substance to be removed | Desired Removal Quantity per day (average) | Maximum Desired Removal Quantity per day |
| --- | --- | --- |
| Urea | 20 grams | 40 grams |
| Phosphorus | 800 milligrams | 1300 milligrams |
| Sulfate | 4.5 grams | 8 grams |
| Uric Acid | 400 milligrams | 600 milligrams |
| β-2-microglobulin | 300 micrograms | 300 milligrams |
| Creatinine | 750 milligrams | 2500 milligrams |

In one embodiment, the portable peritoneal dialysis system can include several stages for cleaning the dialysate, for example two, three, four or more stages, connected in series. In a preferred embodiment, each cleaning stage is achieved by one or more cartridges. The cartridges can be worn or carried by a patient, either on the person, or in a tabletop configuration. In another preferred embodiment, all stages can be small enough to be worn comfortably by a patient in a belt configuration that, preferably, can be concealed under clothing. A pump, such as a battery operated pump, also preferably attached to the belt, circulates the dialysate through each cartridge in a closed loop that includes the patient's peritoneal cavity. In a preferred embodiment, the pump can include a disposable cassette, or a disposable pump head, that integrates with the cleaning stages to form an integrated loop. A disposable cassette or pump head serves to isolate the pump mechanism from the dialysate, enabling the reuse of the pump without the necessity of cleaning and sterilizing the mechanism. Each cleaning stage can perform one or more functions in regenerating the dialysate. One or more identical cartridges can be connected in series, or, alternatively, connected in parallel, for patients that require the removal of larger amounts of uremic solutes. One or more spent cartridges can be replaced by the patient as needed. In a preferred embodiment, the integrated loop can be replaced daily.

FIG. 1 illustrates a specific preferred embodiment of a portable peritoneal dialysis system according to this invention. Each of the components will be described in more detail in the description of each cleaning stage.

A first cleaning stage containing activated carbon and zirconium oxide surrounding semi-permeable fibers can be used to remove organic compounds, phosphorus and/or phosphate, and sulfate. Organic compounds can include, for example, creatinine, p-cresol sulfate, uric acid, and β-2-microglobulin. Organic compounds are usually removed using activated carbon, typically charcoal. Preferably, the activated carbon has a large surface area per unit volume, a wide range of pore sizes for adsorbing various size uremic toxins, and a high purity and/or USP grade. High purity of the carbon can be achieved through multiple acid and/or water washes to remove any water soluble impurities. It is also advantageous for the carbon to be in the form of small granules or a coarse powder for optimal distribution around the fibers and optimal solute transport. Examples of appropriate activated carbon include:

Nuchar® Aquaguard 40 (MeadWestvaco, Glen Allen, Va.), Norit® ROX, and Norit® E Supra (Norit Americas, Marshall, Tex.). A preferred activated carbon is acid-washed pyrolyzed coal-derived activated carbon, such as that marketed by Calgon Carbon Corporation, Pittsburgh, Pa.

Figure 2:
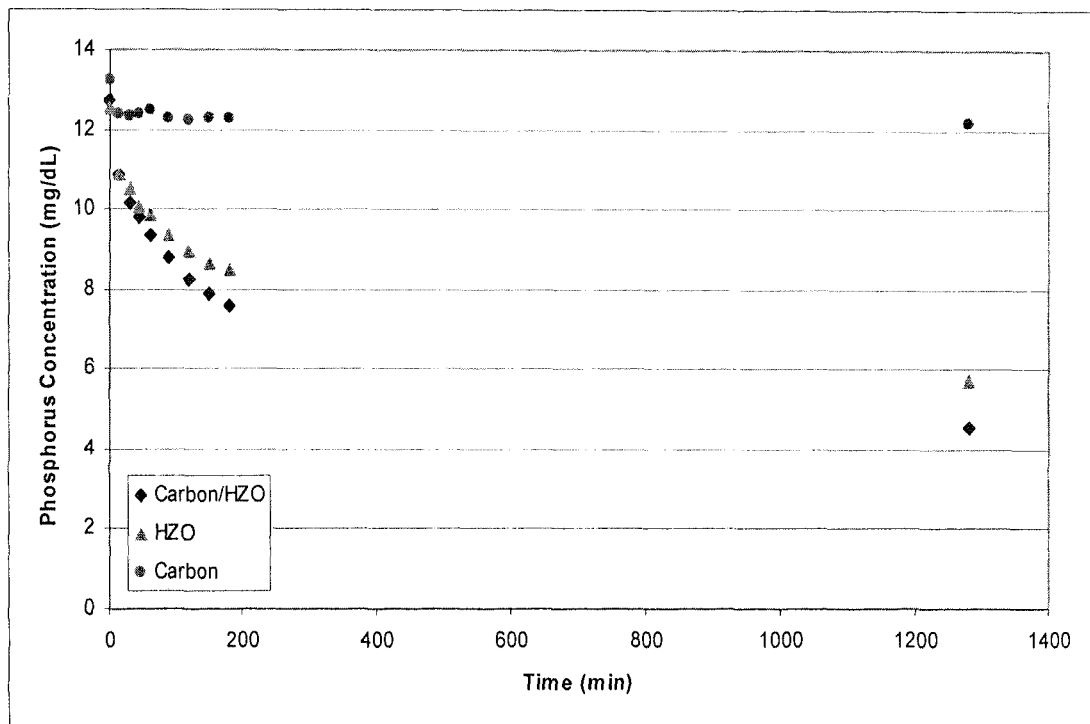
FIG. 2 is a graph of phosphorus concentration as a function of time in a test of phosphorus removal by 3.6 grams of zirconium oxide, 6.2 grams of activated carbon, and a mixture of 3.6 g of zirconium oxide and 6.2 g of activated carbon from a 2 liter volume of solution containing 1.10 grams of sodium phosphate dihydrate and 0.40 grams of anhydrous creatinine.

Phosphorus, as phosphate ($PO_4^{3-}$, $HPO_4^{2-}$, and $H_2PO_4^-$), and sulfate ($SO_4^{2-}$) can be removed by binding to anion exchange resins, or to hydrous zirconium oxide (HZO). Appropriate anion exchange resins include DOWEX™ 1 (hydroxide form), M-43, 21 K XLT, Marathon™ MSA, and M4195 (copper form) (Dow Chemical, Midland, Mich.), and Amberlite™ 96 (Rohm and Haas, Philadelphia, Pa.). In a preferred embodiment, hydrous zirconium oxide (e.g., zirconium oxide in the acetate or carbonate counter ion form) can be used to bind phosphate and sulfate. In a more preferred embodiment, the activated carbon powder can be mixed with the hydrous zirconium oxide powder prior to loading the mixture into the first cartridge. A comparison of phosphorus removal using a mixture of 6.2 grams of activated carbon powder and 3.6 grams of hydrous zirconium oxide, as compared to the same amounts of the separate components was performed, wherein a 2 liter volume solution containing 1.10 grams of trisodium phosphate dihydrate and 0.40 grams of anhydrous creatinine was mixed. The solution was pumped through the hollow fibers of a first stage cartridge at 100 ml/min (milliliters per minute). Samples were removed periodically and analyzed. As illustrated in FIG. 2, hydrous zirconium oxide retains its ability to bind phosphate when mixed with activated carbon.

For efficient uremic solute removal and dialysate transport through the cartridge, the mixture of activated carbon and hydrous zirconium oxide powders can be packed around hollow fibers designed for high rates of diffusive and convective transport of uremic solutes through pores in the fiber walls, and for low resistance to the flow of dialysate through the inside (lumen side) of the hollow fibers. Appropriate hollow fiber materials include cellulose, nylon, polyvinylidene fluoride, polysulfone, polyether sulfone, and polypropylene. A preferred embodiment can include polysulfone hollow fibers with an inner diameter equal to or less than about 210 µm (micrometers), a wall thickness equal to or less than about 40 µm, and an ultrafiltration molecular weight cutoff of about 100 kDa (kilo Daltons), such as, for example, the Optiflux 180 dialyzer (Fresenius Medical Care North America, Waltham, Mass.).

Figure 3:
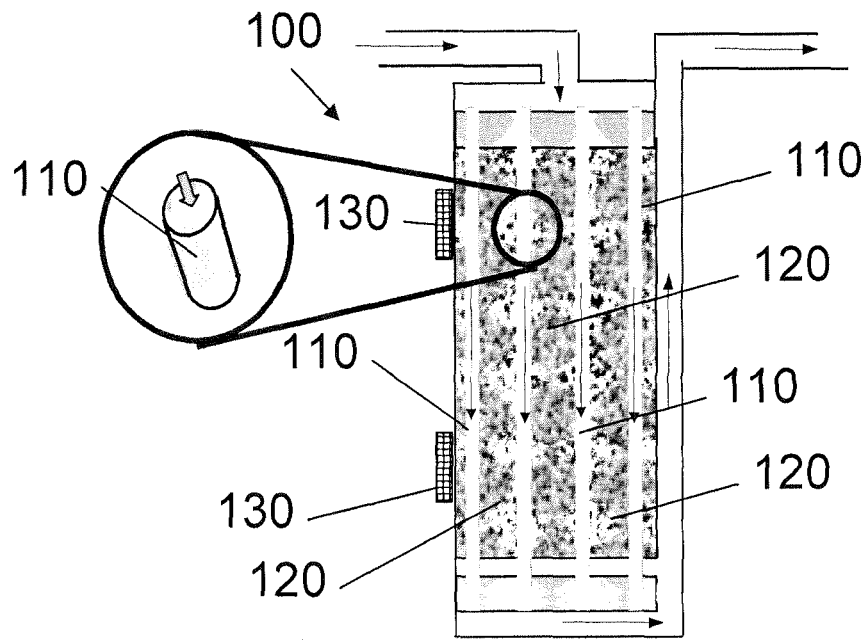
FIG. 3 is a schematic illustration of a first cleaning stage of a portable peritoneal dialysis system according to this invention.
Figure 4:
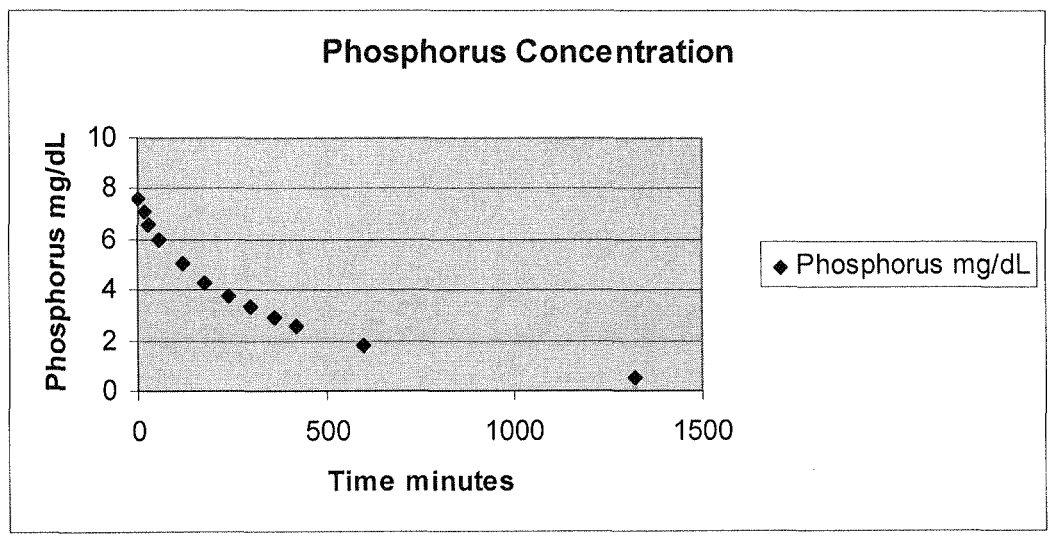
FIG. 4 is a graph of phosphorus concentration as a function of time in a test of phosphorus and creatinine removal by a first stage cartridge from a solution containing 8.0 mg/dL of phosphorus and 12 mg/dL of creatinine.
Figure 5:
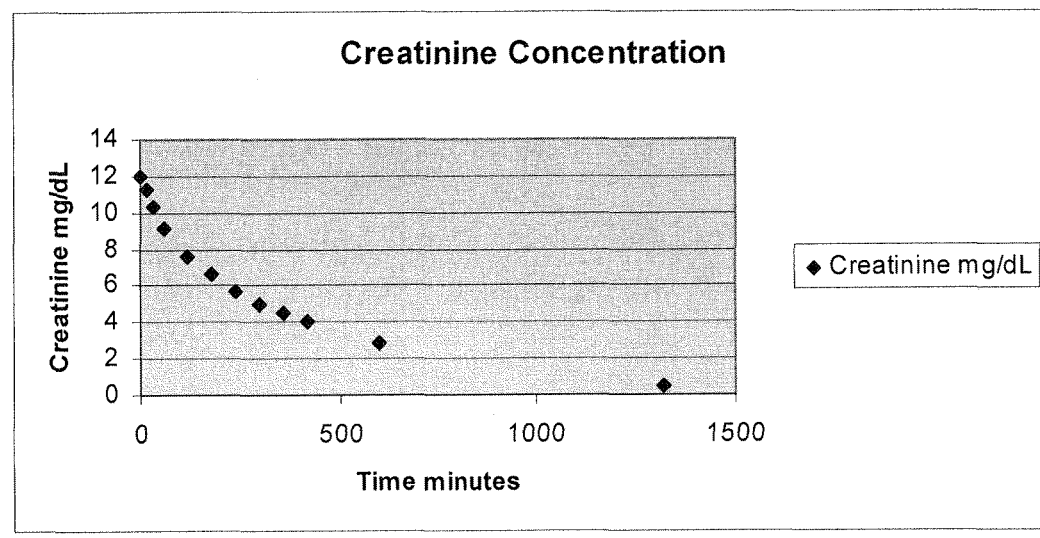
FIG. 5 is a graph of creatinine concentration as a function of time in a test of phosphorus and creatinine removal by a first stage cartridge from a solution containing 8.0 mg/dL of phosphorus and 12 mg/dL of creatinine.

One embodiment of a first stage is illustrated in FIG. 3. Therein, first stage cartridge 100 can include about 4500 hollow fibers 110, of which four fibers are illustrated. The mixture 120 of activated carbon and hydrous zirconium oxide powders is packed around the fibers 110. In a preferred embodiment, the hollow fibers are made of polysulfone, configured to flow at least about 100 ml/min of dialysate with a maximum resulting pressure buildup of about 10 mmHg. The total volume occupied by 4500 polysulfone fibers, excluding potted ends, is about 15-30 cc (cubic centimeters), more preferably about 18 cc, for a total membrane area of 0.21 $m^2$ (square meters). A mixture of about 40-80 g, preferably about 60 g of hydrous zirconium oxide (acetate counter-ion form) and about 30-55 g, preferably about 44 g of activated carbon is mixed uniformly and packed around the polysulfone fibers. The dialysate flows into the inside (lumen side) of fibers 110, and the organic compounds, phosphate, and sulfate pass through the pores of the fibers and are adsorbed on the shell side by the mixture 120 of activated carbon and hydrous zirconium oxide. Any gases displaced by fluid on the shell side are expelled to the atmosphere through hydrophobic vents 130. A hydrophobic vent (e.g., D30480, W. L. Gore & Associates, Newark, Del.) allows gases to pass through but not aqueous liquids. The partially cleaned dialysate then flows out of cartridge 100 to the next cleaning stage. A test of phosphorus and creatinine removal in the first stage was performed, wherein an 8 liter volume solution containing 7.39 grams of $Na_2HPO_4.12H_2O$ and 0.96 grams of anhydrous creatinine was mixed. The mixture was designed to produce a concentration of 8.0 mg/dL (milligrams per deciliter) of phosphorus and 12 mg/dL of creatinine. The solution was pumped through the hollow fibers of a first stage cartridge at 100 ml/minute. Samples were removed periodically and analyzed. The results for phosphorus and creatinine concentrations as a function of time are illustrated in FIGS. 4 and 5, respectively.

A second cleaning stage can be used to remove urea from the dialysate. Urea can be removed by adsorption onto a strong acid cation exchange resin or onto a sorbent, including an ion exchange sorbent, or by initially breaking down the urea into ammonia and carbon dioxide gas with a urea-degrading enzyme followed by removal of the ammonia byproduct by adsorption onto the strong acid cation exchange resin or the sorbent, and venting of the carbon dioxide to the atmosphere. The urea-degrading enzyme can be naturally occurring (e.g., urease from jack beans, other seeds or bacteria), or produced by recombinant technology (e.g., in bacterial, fungal, insect, or mammalian cells that express and/or secrete urea-degrading enzymes), or produced synthetically (e.g., synthesized).

In one embodiment, immobilizing the urease is generally preferred, because immobilization stabilizes the urease while retaining its enzymatic activity, and reduces the likelihood of the urease becoming entrained in the dialysate stream and producing ammonia downstream of the cartridge, away from the ammonia sorbent. Urease can be immobilized by binding it to aluminum oxide, (e.g., SORB, HISORB, Sorb Technology), or to a resin, such as, for example, Amberzyme™ (Rohm and Haas). The enzyme (e.g., urease) may also be chemically attached to the membrane or, alternatively, to porous beads or a resin. This attachment both stabilizes the enzyme for extended use and, in the case of attachment to porous beads or resin, allows the urease to be filled and/or replaced in the device. In particular, urease can be chemically attached to the exterior of the polysulfone hollow fiber membrane or to separate fibers or resins. Attachment can be through reactive pendant groups of amino acid portions of the enzyme such as thiol groups, amino groups, or carboxylic acid groups that will not significantly affect the catalytic site. Chemistries that can be used to immobilize enzymes or cross-linked enzyme crystals (CLECs) are well-known in the art (see e.g., J. Jegan Roy and T. Emilia Abraham, *Strategies in Making Cross-Linked Enzyme Crystals*, Chemical Reviews, 104(9):3705-3721 (2004)). In addition, urease can be used in its crystallized form and be mixed with the ion exchange resin or sorbent, for example, for degradation of the urea. In a preferred embodiment, urease enzyme derived from jack bean meal can be immobilized by cross-linking with polyethylenimine-carbon composite, as described in U.S. application Ser. No. 12/552,332, filed on Sep. 2, 2009.

The ammonia produced in the enzymatic breakdown of urea can be toxic to humans in high concentrations (e.g., above about 2000 µg/dL (micrograms/deciliter)), and also alters the pH away from the physiological pH, inhibiting the enzymatic activity of urease. Therefore, ammonia needs to be removed, and can be removed either by adsorption onto polymeric strong acid cation exchange resins, such as, for example, sulfonic acid substituted polystyrene cross-linked with divinyl benzene, or onto an ion exchange sorbent, such as, for example, zirconium phosphate. Any strong acid cation exchange resin with sufficient ammonia (ammonium ion) binding capacity and purity is suitable. Specific examples of strong acid cation exchange resin include Amberlite™ IRN 77, IRN 97, IRN 99, IR 120, UP 252, CG 15, CG 120, IRC 50, IR 200, and IRA 900 (Rohm and Haas, Philadelphia, Pa.), or comparable resins manufactured by Dow Chemical, Mitsubishi, Purolite, Sybron, and Lanxess.

In a preferred embodiment, the ammonia can be removed by adsorption onto zirconium phosphate. In a more preferred embodiment, zirconium phosphate with improved ammonia binding capacity is prepared as described in U.S. application Ser. No. 12/569,485. An advantageous property of zirconium phosphate is that it helps control the pH in the vicinity of the urease, maintaining it at or near physiological pH, and therefore maintaining the enzymatic activity of the urease.

Polymeric strong acid cation exchange resins or ion exchange sorbents bind ammonia in the form of ammonium ion ($NH_4^+$), and the ability of the resin or sorbent to bind ammonium ion is reduced by competition for binding sites from other positively charged ions (cations), thus requiring larger amounts of ammonia-removing resins or sorbents, and increasing the weight of the cartridge. Therefore, it is preferable to exclude cations other than ammonium ion from the portion of the cartridge that contains the urease and cation exchange resin or zirconium phosphate sorbent. Cation retention in the dialysate has the additional benefit that the patient's system is not overly depleted of essential ions, such as, for example, calcium ($Ca^{+2}$) and magnesium ($Mg^{+2}$).

A preferred approach to cation retention in the dialysate can be to employ hollow fibers that have walls which allow urea to pass through but not significant concentrations of cations. Hollow fibers can be fabricated from or coated with a cation-rejecting material. For example, a layer can be formed on the inside or outside of the hollow fibers by coating or co-extruding them with a cation-rejecting material. The material forming the selective cation-rejecting layer can be, for example, esterified cellulose or acetylcellulose (cellulose acetate). In a preferred embodiment, the selective layer can be acetylcellulose, as described in German Application No. DE 10 2008 003 090.2, filed on Jan. 3, 2008, and published as WO 2009/083260 A1 on Jul. 9, 2009. As disclosed in that application, hollow fibers were produced by the phase inversion process. First, two spinning dope solutions A and B were produced. The first spinning dope solution A comprised the material for the lumen-side selection layer of the hollow fiber membrane and the second spinning dope solution B comprised the material for the support layer.

The spinning dope solution for the support layer (the outer layer) consisted of 20% by weight of Udel 3500 polysulphone and 5% by weight of K90 polyvinylpyrrolidone and also 1% by weight of water, which were in solution in dimethylacetamide. The viscosity of this solution was about 11 500 mPa·s. The spinning dope for the lumen-side selection layer consisted of 30% by weight of cellulose diacetate having a molecular weight of 29 kD (kilo Dalton) and an acetyl content of 40% (available from Sigma/Aldrich). It was dissolved in dimethylacetamide by stirring. The viscosity of this solution was about 15 000 mPa·s.

The two spinning dope solutions were spun in a suitable volume ratio through a composite hollow fiber die as known from the prior art. In the prior art composite hollow fiber die, the two solutions were led through mutually concentric die channels which permit the coextrusion of the inner and outer spinning dopes. The two concentric die channels surrounded an axial channel through which a coagulant for the two spinning dope layers was led. Water was used as inner coagulant.

The temperature of the die pack (spin pack) was 20° C., but could be further varied in the realm of the process. Surprisingly, fibers spun at low temperature (<30° C.) were found to have a higher selectivity of urea over cations such as sodium, potassium, i.e., monovalent cations.

After emerging from the spin pack, the hollow fiber passed through an air gap of about 250 mm before entering a water-filled coagulation bath having a temperature of about 42° C. Subsequently, the composite hollow fiber thus obtained was rinsed in a rinse bath temperature controlled to 75° C. The forwarding speed of the fiber was 250 mm/s. The hollow fiber thus obtained was subsequently dried at about 95° C. Coagulation and rinse bath volumes and forwarding speed were adjusted so as to obtain a solvent-free regular hollow fiber.

The dry fiber was subsequently reeled. A bundle of the hollow fiber consisted of 2300 fibers having a total surface area of 0.4 $m^2$. Fiber internal diameter was 200 μm. Fiber external diameter was 261 μm. The thickness of the selection layer was about 500 nm.

The fibers were moulded into a housing and potted with polyurethane to form a module ensuring independent flows against fiber lumen and against fiber outside surface. The hollow fiber membrane was subsequently investigated in respect of its ultrafiltration rate and also its permeability to urea and various salts.

Aqueous ultrafiltration was determined by applying an overpressure on the lumen side at a temperature of 37° C. and determining the amount of water passing from the lumen side of the hollow fiber to the outside surface of the hollow fiber. The ultrafiltration rates measured for the membrane were in the range from 0.1 to 0.3 (ml/(h Torr $m^2$)).

Urea and salt permeabilities were determined using 500-700 ml of a urea-containing salt solution comprising 25 mM urea, 141 mM NaCl, 2.5 mM $CaCl_2$, 249 mM glucose and recirculated through the hollow fiber on the lumen side at 50 ml/min.

The solution on the lumen side of the hollow fiber was situated in a pressure-tight sealed receptacle, so that the volume of the test solution could not change during the experimental period. A 538 mM glucose solution was pumped on the outside surface of the membrane in countercurrent at a flow rate of 50 ml/min.

After two hours at room temperature, a sample of the solution circulating on the lumen side was taken and analysed with a commercially available analyser (Cobas Integra 400, Hoffmann-La Roche, Diagnostics Div., Basel, Switzerland). The concentrations of the analysed starting solution can be used to calculate membrane permeability and selectivity. The membrane gave the results for the removal of the aforementioned urea-containing solution shown in Table 2.

TABLE 2

Permeability and selectivity of cellulose acetate membrane

|  | Sodium | Urea | Calcium |
| --- | --- | --- | --- |
| Initial value (mM) | 158 | 25 | 2.8 |
| Value after 2 h (mM) | 157 | 15 | 3.0 |

The coefficient of variation of the measurement was 1% for sodium, 3.5% for calcium and 1.8% for urea. As is evident from the measurements, urea is efficiently removed by the hollow fiber membrane of the invention, whereas sodium and calcium are substantially retained.

The membrane was further characterized by means of permeation tests with pure gases. To this end, an overpressure of about 1 bar of the gas was applied to the hollow fiber on the lumen side and the resulting gas flux across the membrane was measured. Table 3 shows a typical result.

TABLE 3

Gas flux through inventive membrane at room temperature and an across-membrane pressure gradient of 1 bar.

|  | Nitrogen | Carbon dioxide |
|---|---|---|
| Gas flux (ml/(h Torr m$^2$)) | 0.1 | 15 |

These results show that the membrane has only very few pores, since customary fluxes through conventional membranes are typically on the order of several liters/(h Torr m$^2$).

Alternatively, the cation-rejecting material can be a thin film composite membrane, wherein an interfacial polymerized coating is deposited on the surface of an existing membrane. An interfacial polymerized coating can be deposited by flowing an aqueous solution of a compound containing more than one amine group, such as, for example, p-phenylenediamine, through the inside of a hollow fiber, followed by flowing a non-aqueous solution of an acid chloride containing two or more carbonyl groups and capable of forming a covalent bond with amine, such as, for example, trimesoyl chloride, through the inside of the hollow fiber. In a preferred embodiment, about 0.2-2.0%, more preferably about 2.0% by weight of p-phenylenediamine dissolved in water, followed by about 0.5-2.0%, more preferably about 2.0% by weight of trimesoyl chloride dissolved in hexane, can be used to make a thin film composite membrane on the lumen side of a polysulfone hollow fiber with an ultrafiltration molecular weight cutoff equal to or less than about 50 kDa, an internal diameter equal to or less than about 210 μm, and a wall thickness equal to or less than about 40 μm.

Retaining cations in the dialysate, while having the advantages discussed above, can also generate an osmotic pressure across the hollow fiber wall, due to the concentration of dissolved solutes in the dialysate, that needs to be balanced on the shell side, which is the side of the fiber wall containing the urease and ammonia sorbent. Otherwise, liquid will be driven to flow into the lumen side of the hollow fibers, drawing air through the vent that is used to exhaust carbon dioxide and other gases from the shell side of the cartridge. The rate of diffusion of urea through air is much lower than the rate of diffusion through liquid, and therefore, for efficient mass transfer of urea within the urease and ammonia sorbent material, the shell side is preferably filled with liquid. Osmotic pressure can be balanced with a substance that is non-toxic, does not react with the urease or ammonia sorbent, and, most importantly, has a high enough molecular weight that it does not cross the membrane wall into the lumen side of the hollow fiber. Appropriate osmotic agents include sucrose and other polysaccharides, such as, for example, polydextrin and icodextrin, and raffinose. A preferred osmotic agent is sucrose, because it is not substantially transported across the cation-rejecting hollow fiber walls. In a preferred embodiment, the osmotic agent can be mixed in with the strong acid cation exchange resins or sorbents.

Figure 6:
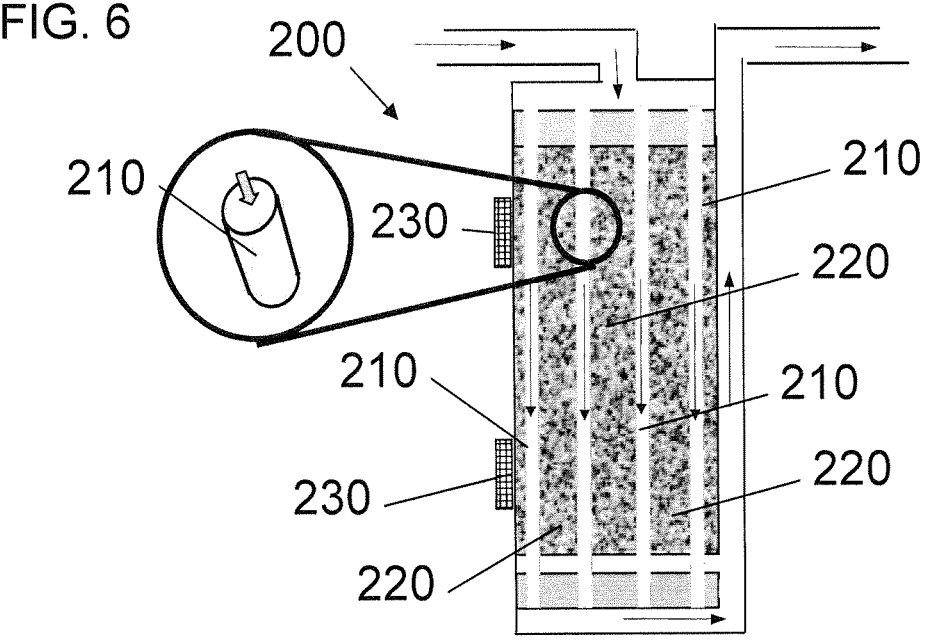
FIG. 6 is a schematic illustration of a second cleaning stage of a portable peritoneal dialysis system according to this invention.

One embodiment of a second stage cartridge is illustrated in FIG. 6. Therein, second stage cartridge 200 can include about 4500 cation-rejecting hollow fibers 210, of which four fibers are illustrated. In a preferred embodiment, the cation-rejecting hollow fibers can be made of polysulfone, with a cation-rejecting thin film composite membrane coated on the lumen side (inside) of the hollow fibers. The mixture 220 of urease, ammonia sorbent, and sucrose can be packed around the fibers 210 on the shell side of the second stage cartridge 200. The hollow fibers are configured to flow at least about 100 ml/min of dialysate with a maximum resulting pressure buildup of about 10 mmHg. The total volume occupied by 4500 polysulfone fibers, excluding potted ends, is about 15-30 cc, more preferably about 18 cc, for a total membrane area of 0.21 m$^2$. A mixture of about 10 cc of cross-linked jack bean urease immobilized on polyethylenimine-carbon composite and about 110 cc of ammonia binding resin (sulfonic acid substituted polystyrene cross-linked with divinyl benzene) or zirconium phosphate is packed around the polysulfone fibers, for a total packed bed volume of about 138 cc.

In a more preferred embodiment, two urea-removing cartridges as previously described can be connected in series, as illustrated in FIG. 1. As illustrated in FIG. 6, in second stage cartridge 200, the dialysate flows into the inside (lumen side) of fibers 210, and the urea passes through the fibers and is broken down on the shell side by the immobilized urease into ammonia and carbon dioxide. The ammonia is adsorbed by the ammonia binding resin, and carbon dioxide and other gases on the shell side are expelled to the atmosphere through hydrophobic vents 230. The partially cleaned dialysate then flows out of cartridge 200 to the next cleaning stage.

Figure 7:
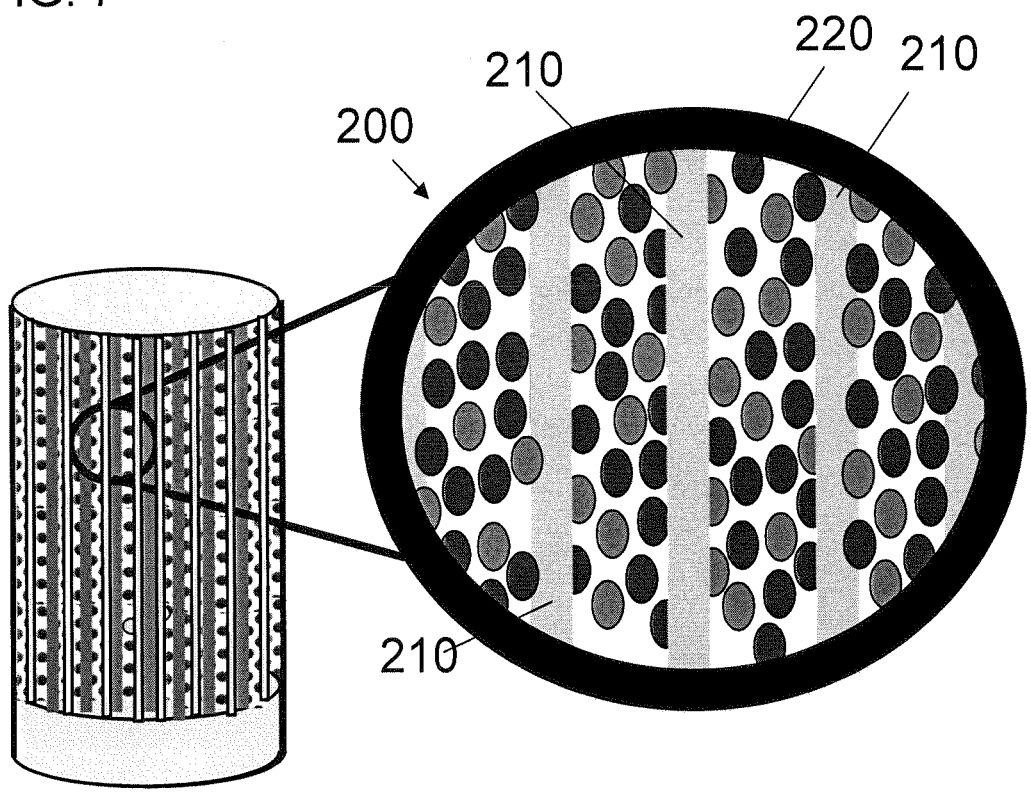
FIG. 7 is an exploded partial cross-sectional view of the interior of the second cleaning stage of a portable peritoneal dialysis system illustrated in FIG. 6.
Figure 8:
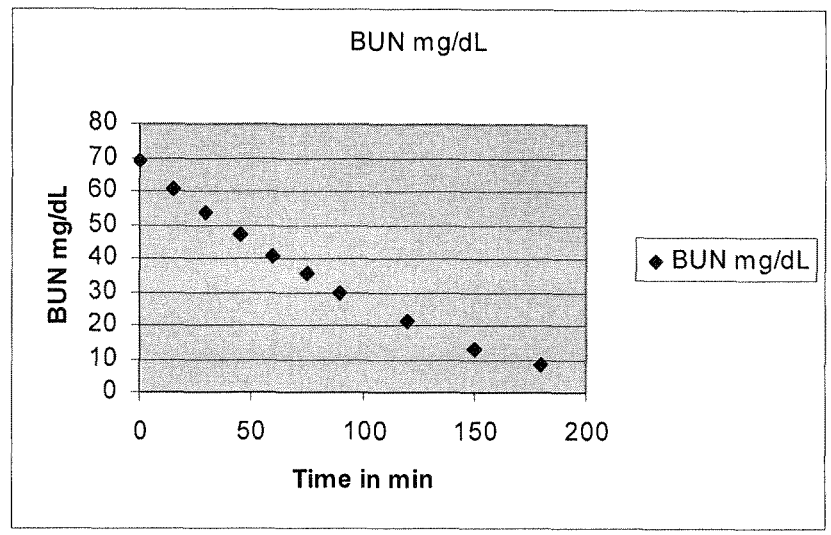
FIG. 8 is a graph of blood urea nitrogen (BUN) concentration as a function of time in a test of urea and ammonia removal by a second stage cartridge containing 141 g of zirconium phosphate and 5 g of immobilized urease composite.
Figure 9:
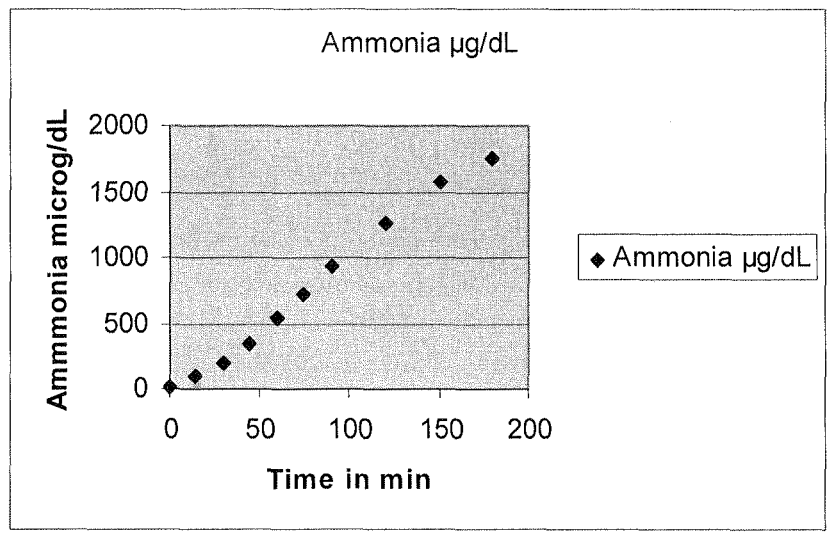
FIG. 9 is a graph of ammonia concentration as a function of time in a test of urea and ammonia removal by a second stage cartridge containing 141 g of zirconium phosphate and 5 g of immobilized urease composite.

FIG. 7 is an exploded partial cross-sectional view of a cartridge 200 illustrating the cation-rejecting hollow fibers 210, and the mixture 220 of immobilized urease, ammonia sorbent resin, and sucrose on the shell side of the cartridge. A test of urea and ammonia removal in the second stage was performed, wherein a second stage cartridge contained 141 grams of zirconium phosphate that was blended with 5.0 grams of ground cross-linked jack bean meal immobilized urease composite. The cartridge contained about 4500 polysulfone hollow fiber membranes, described above, with a total membrane area of 0.21 m$^2$, and without cation-rejecting modifications. A solution of 1.50 grams of urea was dissolved in 1 liter of deionized water. The solution was circulated through the cartridge at 100 ml/min and back to the beaker. As demonstrated by the results, the urease rapidly hydrolyzed the urea and the zirconium phosphate bound most of the ammonia that was produced, maintaining the ammonia concentration below 2000 μg/dL. The experiment also demonstrated that under these conditions, the sorbent was wetted quickly (under 5 minutes) and that the urea crossed the membrane to the shell side where it could react. FIGS. 8 and 9 illustrate the blood urea nitrogen (BUN) concentration and the ammonia concentration, respectively, as a function of time in this experiment. Although technically a misnomer, the term BUN is widely known in the art, and refers to the amount of nitrogen, usually in blood serum or plasma, present in the form of urea. The BUN measurement can be made for other liquids, such as, for example, dialysate.

Figure 10:
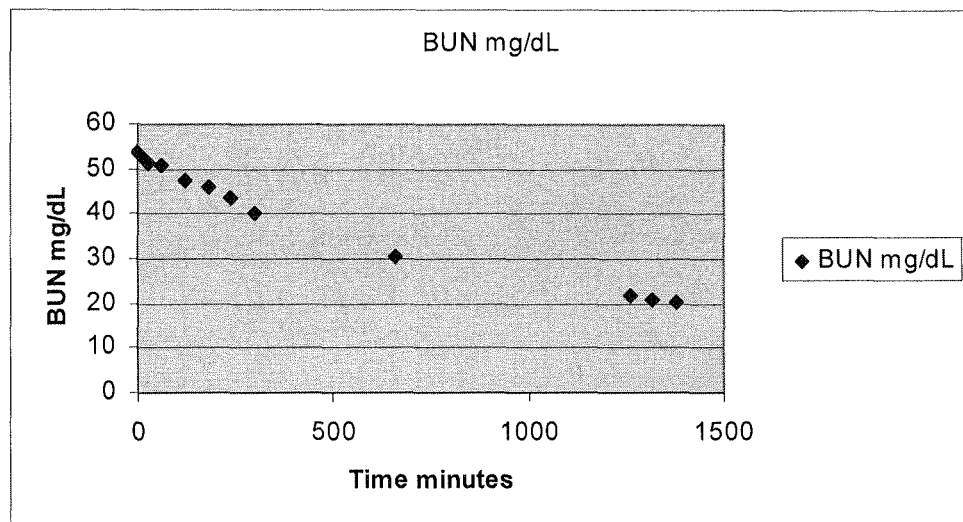
FIG. 10 is a graph of blood urea nitrogen (BUN) concentration as a function of time in a test of urea and ammonia removal by a second stage cartridge containing 132 g of zirconium phosphate and 5 g of immobilized urease composite.
Figure 11:
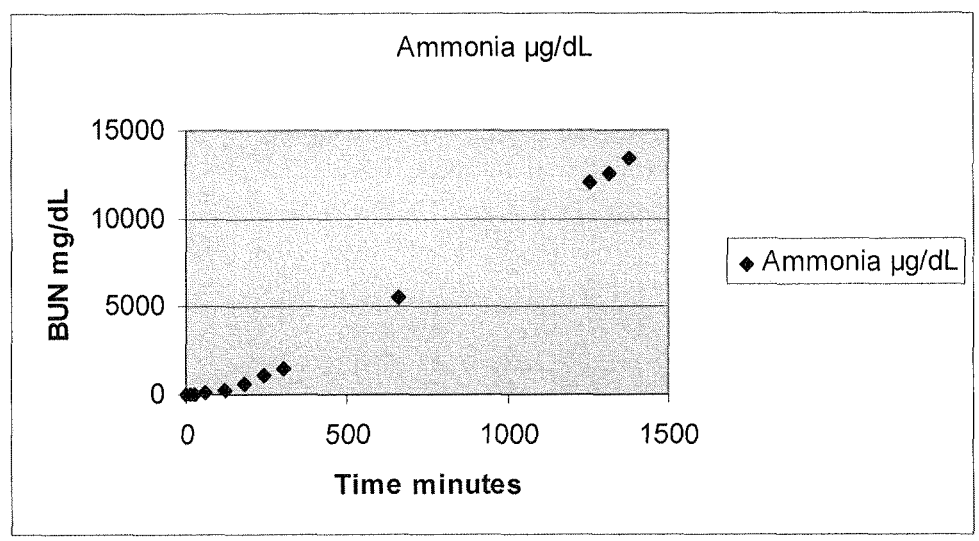
FIG. 11 is a graph of ammonia concentration as a function of time in a test of urea and ammonia removal by a second stage cartridge containing 132 g of zirconium phosphate and 5 g of immobilized urease composite.

A second experiment used a similar cartridge. It had slightly less zirconium phosphate (132 grams) and 5.0 grams of immobilized urease composite. A significantly larger volume of solution was used (8 liters), and much more total urea (9.6 grams). Since, preferably, two cartridges of this type would be used in the portable peritoneal dialysis system, the 9.6 grams is comparable to the amount of urea that a single cartridge in the device might be exposed to with a patient. With a flow rate of only about 100 ml/min, more than one hour was required to circulate the entire volume of solution. Some time between 5 and 11 hours into the experiment, the concentration of ammonia exceeded the level that is considered safe to return to the patient (about 2000 μg/dL). With an additional equivalent cartridge and a third cartridge containing only zirconium phosphate, the ammonia level would be expected to be maintained below about 2000 μg/dL. During the experiment, more than half the urea was hydrolyzed. FIGS. 10 and 11 illustrate the blood urea nitrogen (BUN) concentration and the ammonia concentration, respectively, as a function of time in this experiment.

Figure 12:
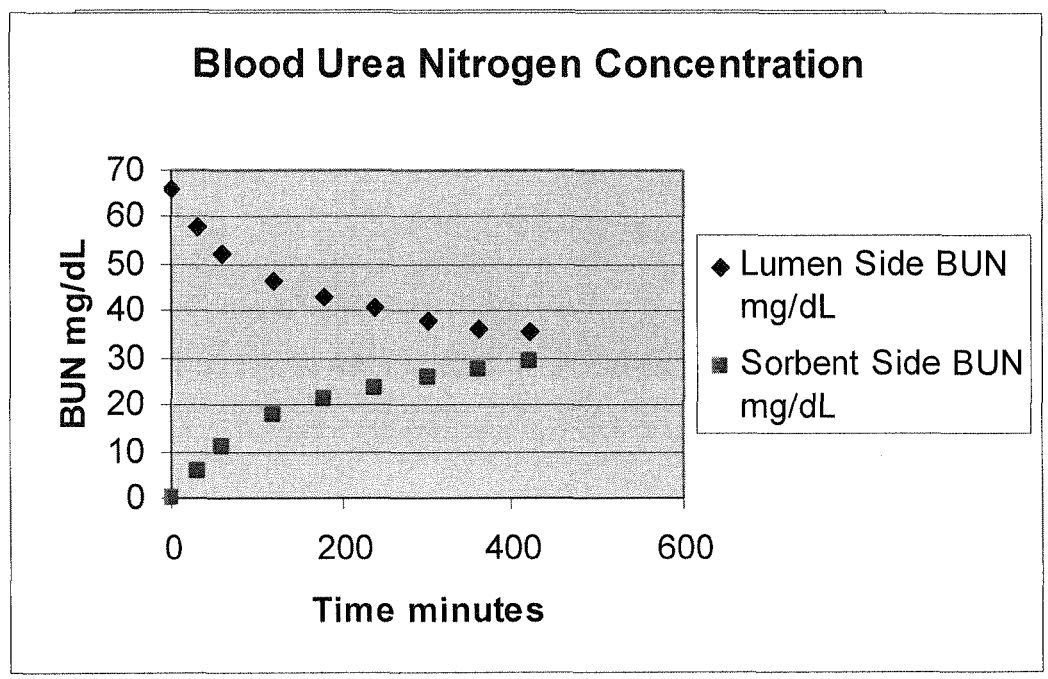
FIG. 12 is a graph of blood urea nitrogen (BUN) concentration as a function of time in a test of urea and cation transport across thin film composite membrane hollow fibers of a second stage cartridge.
Figure 13:
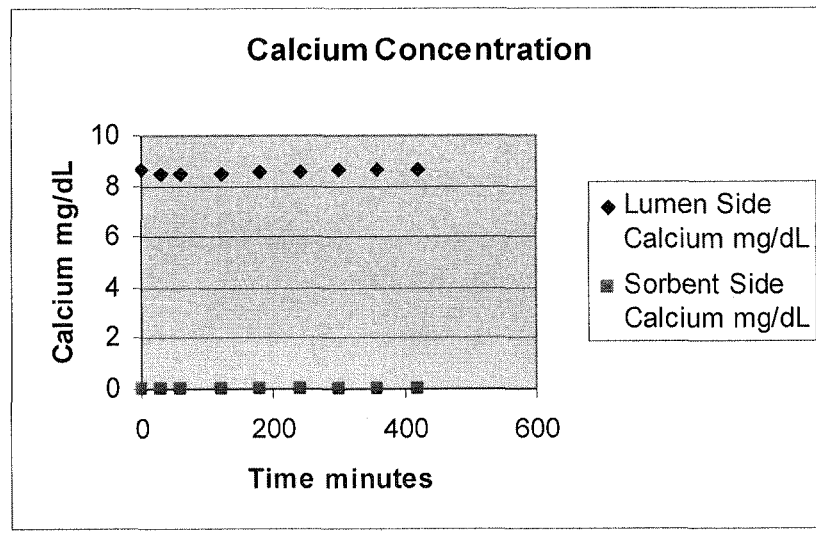
FIG. 13 is a graph of calcium ($Ca^{+2}$) concentration as a function of time in a test of urea and cation transport across thin film composite membrane hollow fibers of a second stage cartridge.
Figure 14:
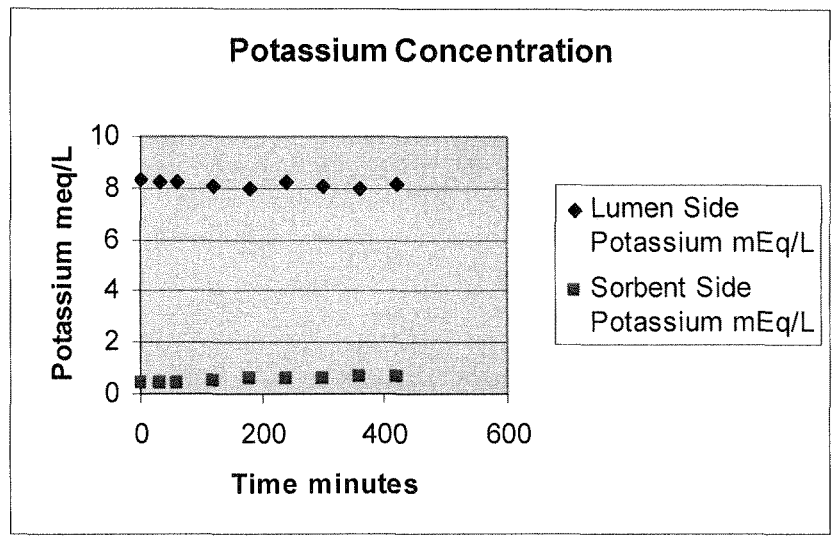
FIG. 14 is a graph of potassium ($K^+$) concentration as a function of time in a test of urea and cation transport across thin film composite membrane hollow fibers of a second stage cartridge.
Figure 15:
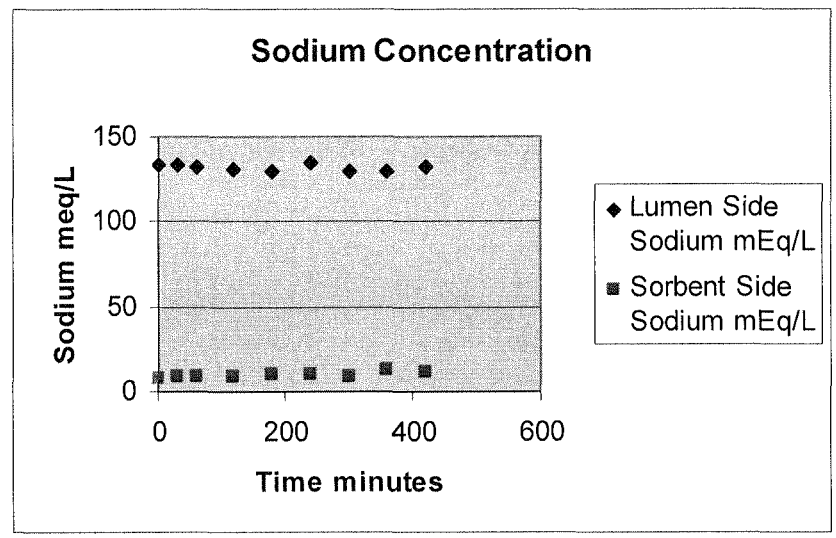
FIG. 15 is a graph of sodium ($Na^+$) concentration as a function of time in a test of urea and cation transport across thin film composite membrane hollow fibers of a second stage cartridge.

To measure the cation-rejecting properties of thin film composite membranes, two solutions were mixed in beakers and pumped counter current to each other at about 100 ml/min through a cartridge containing about 4500 polysulfone hollow fibers, described above, with a total membrane area of 0.62 m$^2$, and including cation-rejecting thin film composite membranes on the lumen side, prepared as described above. The lumen side solution consisted of 30.85 grams sodium chloride, 1.36 grams of calcium chloride dihydrate, 2.42 grams of potassium chloride, and 6.00 grams of urea dissolved in 4.00 liters of deionized water. The sorbent side contained 195.6 grams of D-glucose (calculated to approximately balance osmotic pressure) in 4 liters of deionized water. As expected, urea crossed the membrane. Within the accuracy of the analyzer, only a trace of sodium crossed, and no calcium or potassium crossed. Values of 10 mEq/L (milliequivalents per liter) for sodium, 1.0 mEq/L potassium, and 0.2 mg/dL for calcium were considered the low limits of accurate measurement for the analyzer used to detect sodium, potassium, and calcium in this experiment. FIG. 12 illustrates the blood urea nitrogen (BUN) concentration as a function of time, that started from a high concentration on the lumen side (dialysate side) and a low concentration on the sorbent side, and then, as the urea crossed the cation-rejecting membrane, the urea concentrations on each side of the membrane became nearly equal, because there was no urea removal in this experiment. FIGS. 13-15 illustrate that the concentrations of the cations calcium, potassium, and sodium, respectively, remained high on the lumen side and low on the sorbent side of the membrane, because the cation-rejecting membrane was preventing cations from crossing over from the lumen side to the sorbent side.

Figure 16:
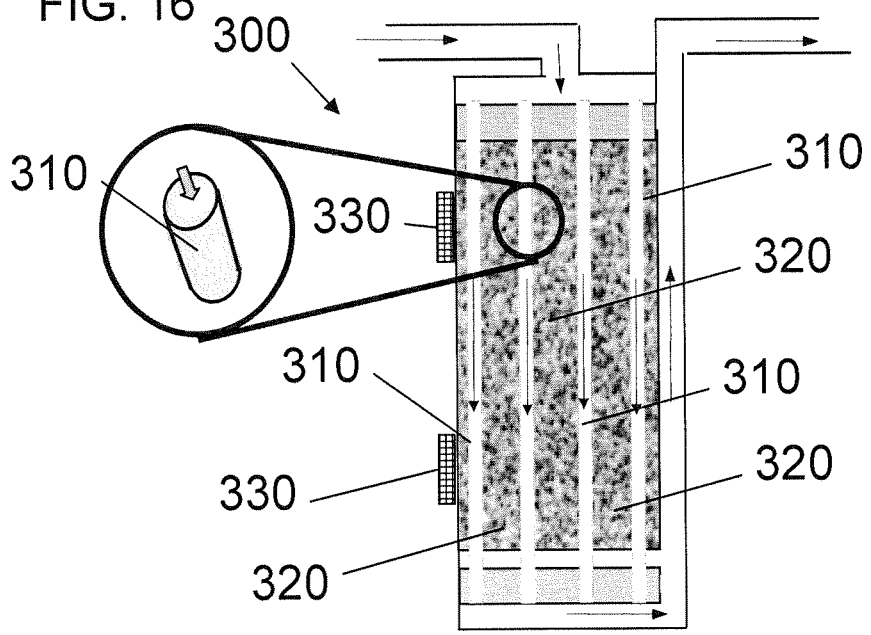
FIG. 16 is a schematic illustration of a third cleaning stage of a portable peritoneal dialysis system according to this invention.

The immobilized urease composite in a second stage cartridge can be packed up to the outlet of the cartridge, and therefore some ammonia can be released into the dialysate and not removed by contact with the ammonia binding resin or sorbent. Therefore, a third optional cleaning stage can be used to remove any remaining ammonia from the dialysate, by using the same cation-rejecting fibers and ammonia binding resin or sorbent described above, but without urease. One embodiment of a third stage cartridge is illustrated in FIG. 16. Therein, third stage cartridge 300 can include about 4500 cation-rejecting hollow fibers 310, of which four fibers are illustrated. The ammonia binding resin or sorbent 320 is packed around the fibers 310. In a preferred embodiment, the cation-rejecting hollow fibers can be made of polysulfone, and include cation-rejecting thin film composite membranes on the lumen side, prepared as described above. The total volume occupied by the polysulfone fibers, excluding potted ends, is about 15-30 cc, more preferably about 18 cc, for a total membrane area of 0.21 m$^2$. About 120 cc of ammonia binding resin (sulfonic acid substituted polystyrene crosslinked with divinyl benzene) mixed with sucrose is packed around the cation-rejecting polysulfone fibers, for a total packed bed volume of about 138 cc. The dialysate flows into the inside (lumen side) of fibers 310, and the ammonia is adsorbed by the ammonia binding resin 320. Any gases displaced by fluid on the shell side are expelled to the atmosphere through hydrophobic vents 330. The partially cleaned dialysate then flows out of cartridge 300 to the next cleaning stage.

Figure 17:
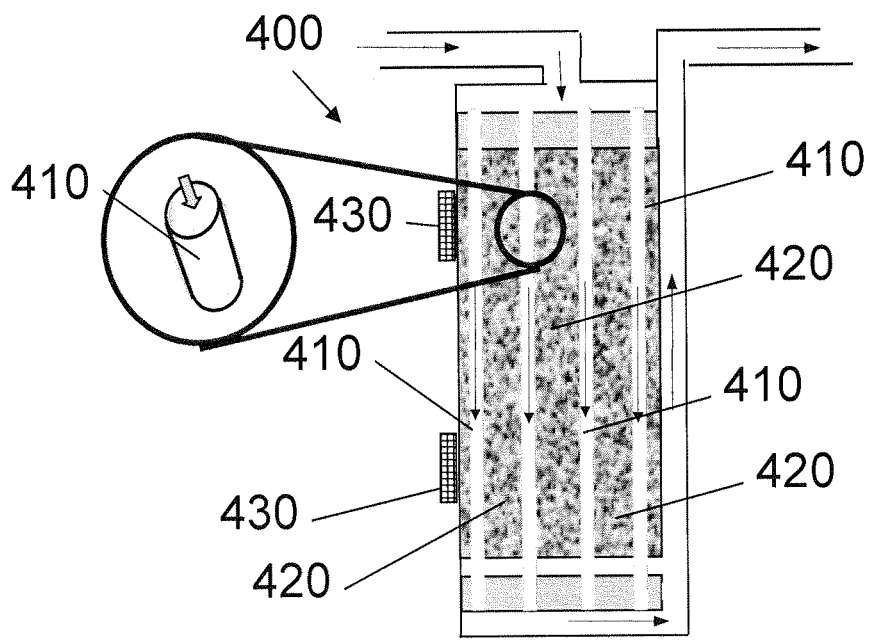
FIG. 17 is schematic illustration of a fourth cleaning stage of a portable peritoneal dialysis system according to this invention.

A fourth optional cleaning stage can be used to remove any remaining organic compounds, phosphorus, and sulfate, and to insure that the dialysate is at the normal physiological pH of about 7.4 before the regenerated dialysate is returned to the patient. The fourth stage cartridge can be similar to or identical to the first stage cartridge described above, or the fourth stage cartridge can include a mixture of hydrous zirconium oxide and sodium zirconium carbonate mixed with activated carbon. Mixtures of hydrous zirconium oxide and sodium zirconium carbonate with improved pH control are described in U.S. Pat. No. 6,627,164, issued on Sep. 30, 2003. Alternatively, the fourth stage cartridge can include a pH adjusted mixed bed ion exchange resin (e.g., IRN 150, Rohm and Haas), mixed with activated carbon. In one embodiment, illustrated in FIG. 17, the fourth stage cartridge can be identical to the first stage cartridge. Therein, fourth stage cartridge 400 can include about 4500 hollow fibers 410, of which four fibers are illustrated. The mixture 420 of activated carbon and hydrous zirconium oxide powders is packed around the fibers 410. In a preferred embodiment, the hollow fibers can be made of polysulfone, configured to flow at least about 100 ml/min (milliliters per minute) of dialysate with a maximum resulting pressure buildup of about 10 mmHg. The total volume occupied by 4500 polysulfone fibers, excluding potted ends, is about 15-30 cc (cubic centimeters), more preferably about 18 cc, for a total membrane area of 0.21 m$^2$. A mixture of about 40-80 g, preferably about 60 g of hydrous zirconium oxide (acetate counter-ion form) and about 30-55 g, preferably about 44 g of activated carbon is mixed uniformly and packed around the polysulfone fibers. The dialysate flows into the inside (lumen side) of fibers 410, and the organic compounds, phosphate, and sulfate pass through the pores of the fibers and are adsorbed on the shell side by the mixture 420 of activated carbon and hydrous zirconium oxide. Any gases displaced by fluid on the shell side are expelled to the atmosphere through hydrophobic vents 430. The substantially cleaned dialysate then flows out of cartridge 400 back to the patient's peritoneal cavity.

Thus, after flowing through the replaceable cartridges of the portable peritoneal dialysis system, the dialysate has been regenerated and is ready for reuse. The dialysate is substantially free of urea, uric acid, and creatinine, and has lower levels of phosphate and sulfate. Due to the design of the urea-removing stage such that its components reject cations, the dialysate retains sufficient levels of calcium and magnesium ions, eliminating the need for a mechanism to replace these ions in the patient. In addition, repelling cations like sodium and potassium prevents the ions from entering the shell-side of the second and third stage replaceable cartridges, decreasing the load of ions bound to the shell-side of the second and third stage cartridge components (e.g., the cation exchange resin or sorbent) and the frequency at which the cartridges need to be replaced/regenerated. Thus, the rejection of sodium and potassium increases the longevity and reduces the size and weight of the second and third stage replaceable cartridges.

The portable peritoneal dialysis system can have one or more access ports for coupling to the closed loop liquid system to provide inflow to and outflow from the patient's peritoneal cavity, where the access ports can include medically appropriate plastic tubing, a double lumen catheter or two single lumen catheters. The portable peritoneal dialysis system also contains a volume of peritoneal dialysis solution (dialysate) that is infused into and out of the patient's peritoneal cavity such that the peritoneal dialysis solution removes uremic waste metabolites that diffuse through the patient's peritoneal membrane into the peritoneal dialysis solution. Preferably, the system continuously circulates the peritoneal dialysis solution for maximum mass transport of the uremic toxins across the peritoneal membrane, although periodic dwell times without circulation could also be advantageous for fluid removal. A preferred method of use of the portable peritoneal dialysis system during one dialysis cycle can include infusing a volume of dialysate into the patient's peritoneal cavity, waiting for a dwell time of about 2 hours, draining a volume of dialysate approximately equal to the volume of fluid (ultrafiltrate) accumulated in the patient's peritoneal cavity during the dwell time, typically about 0.8 liters, circulating the dialysate through the portable peritoneal dialysis system continuously for about 8 hours, draining the entire volume of dialysate, infusing another volume of dialysate into the patient's peritoneal cavity, waiting for a dwell time of about 2 hours, and then draining the dialysate out of the patient's peritoneal cavity, leaving the cavity relatively dry for about 12 hours before beginning another peritoneal dialysis cycle. It will be noted the portable peritoneal dialysis system circulates dialysate for a portion of the peritoneal dialysis cycle, but the cycle also includes periods when the dialysate is not being circulated. This type of cycle is referred to herein as semi-continuous operation of the portable peritoneal dialysis system.

A variety of peritoneal dialysis solutions can be used (e.g., Delflex), these solutions being commercially available (e.g., Fresenius Medical Care North America, Waltham, Mass.) and well-known in the art. A volume of about 0.5 to 3 liters of peritoneal dialysis solution can be introduced into the portable peritoneal dialysis system and it is preferable that about 2.5 liters of the solution be infused. Preferably, some fresh peritoneal dialysis solution can be added to the portable peritoneal dialysis system at a convenient time. The peritoneal dialysis solution can also comprise a material added to the solution that binds uremic toxins attached to proteins in the serum. For example, albumin can be added to the peritoneal dialysis solution to aid in the removal of these protein-bound toxins.

The dialysate is circulated through the portable peritoneal dialysis system by a pump. The pump is preferably small in size, preferably about the same size as a cartridge, light weight, capable of at least about 12 hour battery operation for portability, and capable of delivering a sufficient flow rate, typically about 100 ml/min, at system pressure, typically about 50-60 mmHg (millimeters of mercury), and, preferably, including the ability to sterilize the components that contact the dialysate, or, more preferably, including the ability to replace those components with new sterile components without having to replace the entire pump. Appropriate pumps can include the Xavitech V1500 and P1500 (Xavitech, Härnösand, Sweden), or a piezo-electric diaphragm pump, or a disposable cassette pump as described in PCT Application No. PCT/US2007/077119, filed on Aug. 29, 2007. A disposable cassette serves to isolate the pump mechanism from the dialysate, enabling the reuse of the pump without the necessity of cleaning and sterilizing the mechanism.

To consistently and efficiently remove uremic waste metabolites from a patient, control of the portable peritoneal dialysis system and, in particular, the pump flow rates and the timing and sequencing of the components of the dialysis system can be electronically controlled. In a preferred embodiment, the control mechanism can be a microprocessor which can be part of a control unit in the dialysis system. In a more preferred embodiment, the portable peritoneal dialysis system can include an ammonia sensor, integrated with the control system, that controls the pump and stops the flow of the dialysate through the system when the ammonia concentration in the dialysate exceeds the level that is safe to return to the patient, typically about 2000 µg/dL. In an even more preferred embodiment, the portable peritoneal dialysis system can further include a bypass solenoid, controlled by the microprocessor, that directs the dialysate back through the cleaning stages, bypassing the patient, for additional ammonia removal to a safe level, such as below about 2000 µg/dL, prior to returning the dialysate to the patient's peritoneal cavity.

Figure 18:
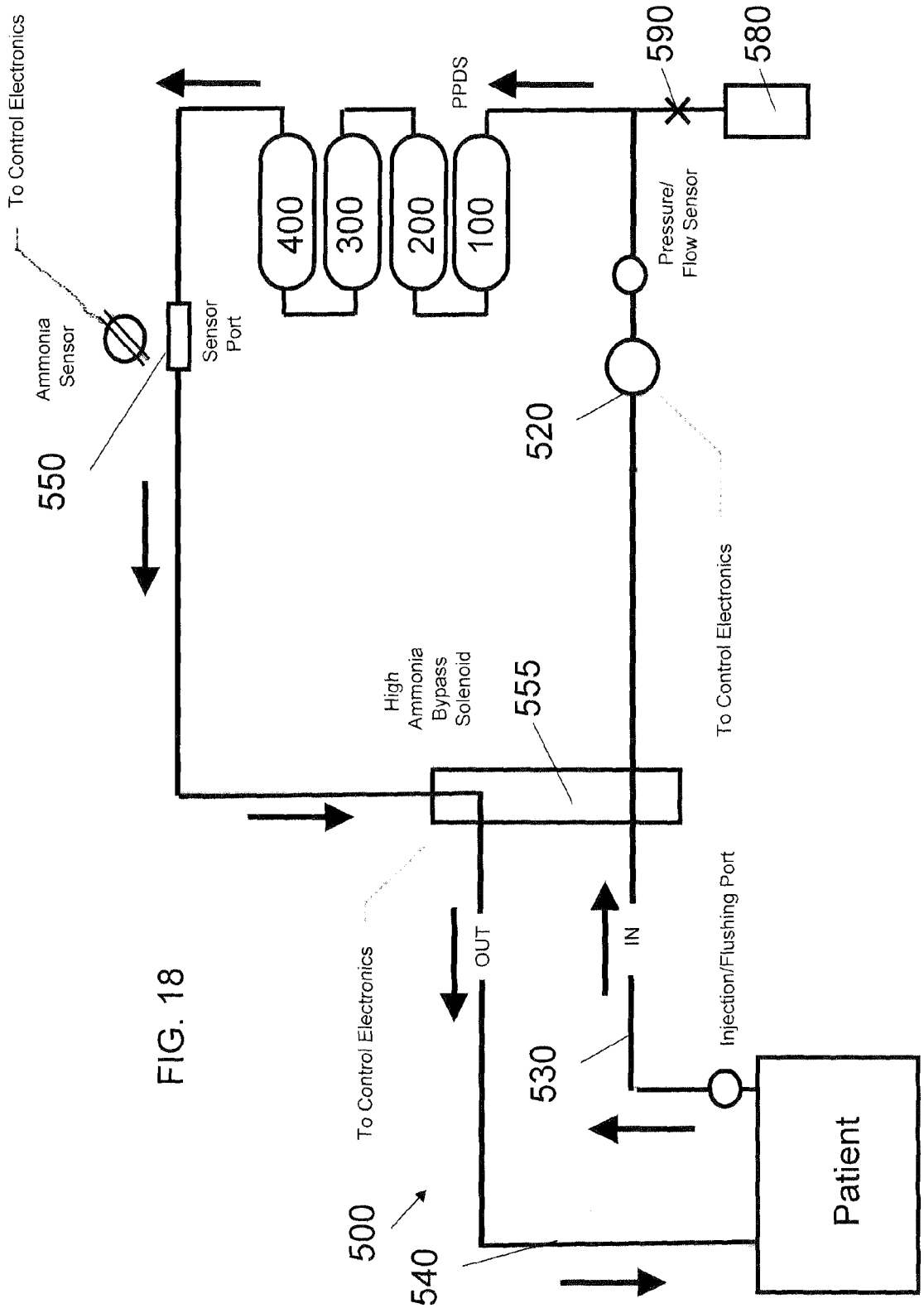
FIG. 18 is a schematic flow diagram of one embodiment of the portable peritoneal dialysis system according to this invention.

A flow diagram of the portable peritoneal dialysis system is illustrated in FIG. 18. Therein, in a preferred embodiment, the portable peritoneal dialysis system 500 can include a pump 520 that pumps the dialysate through first stage cartridge 100, second stage 200, third stage cartridge 300, and fourth stage cartridge 400. The dialysate enters the system through inlet tube 530 and exits the system through outlet tube 540, after passing through the optional ammonia sensor 550. In a more preferred embodiment, the peritoneal dialysis system 500 can include a bypass solenoid 555, triggered by the ammonia sensor 550 or controlled by a microprocessor, that directs the dialysate back through cleaning stages 100-400, bypassing the patient, for additional ammonia removal to a level below 2000 µg/dL prior to returning the dialysate to the patient's peritoneal cavity. In another embodiment, the peritoneal dialysis system 500 can include a drain container 580 for draining fluid (ultrafiltrate) buildup in the patient's peritoneal cavity. The drain container can be controlled by on/off valve 590 that can be operated manually or controlled by a microprocessor. The microprocessor can also control other aspects of the operation of the portable peritoneal dialysis system.

Figure 19:
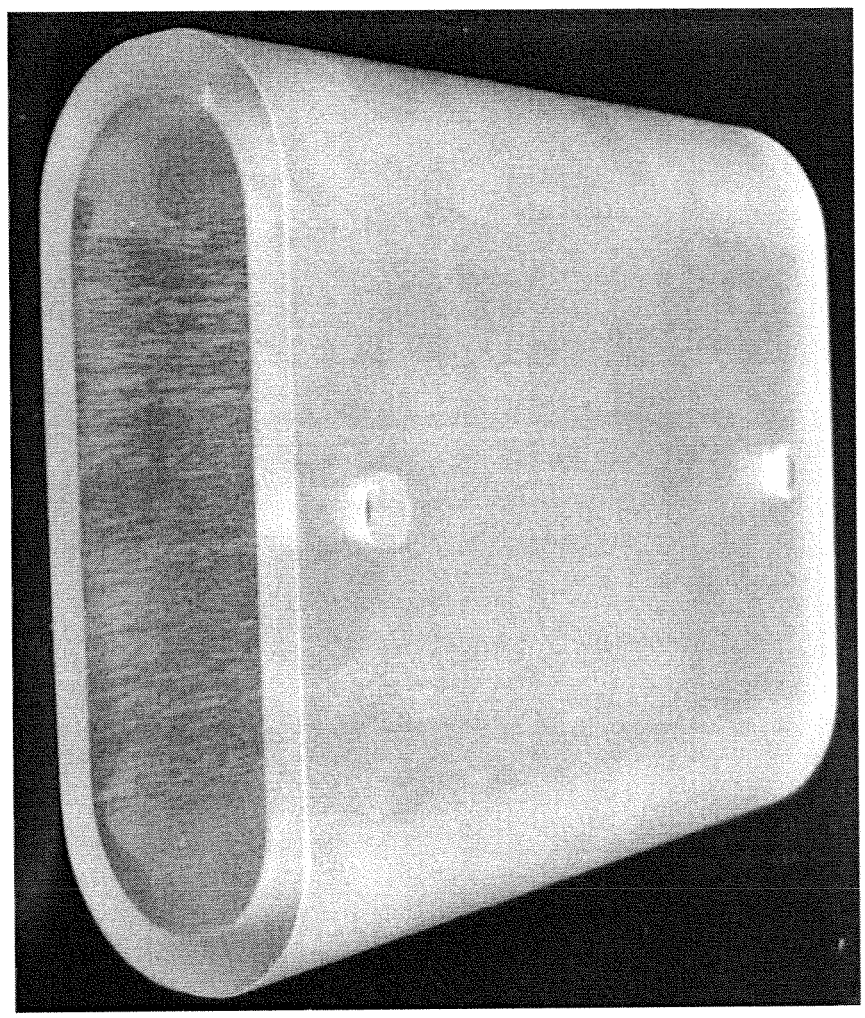
FIG. 19 is a photograph of a cartridge shell of a "racetrack" design for a cleaning stage.

The cartridges can be made of any sufficiently strong and lightweight material that will not contaminate the dialysate. Appropriate materials can include metal, plastic and carbon composite materials. A preferred material is polycarbonate. A preferred design, illustrated in FIG. 19, can employ a flattened oval "racetrack" design that is more comfortable to wear in a belt than a cylindrical "can" design.

Figure 20:
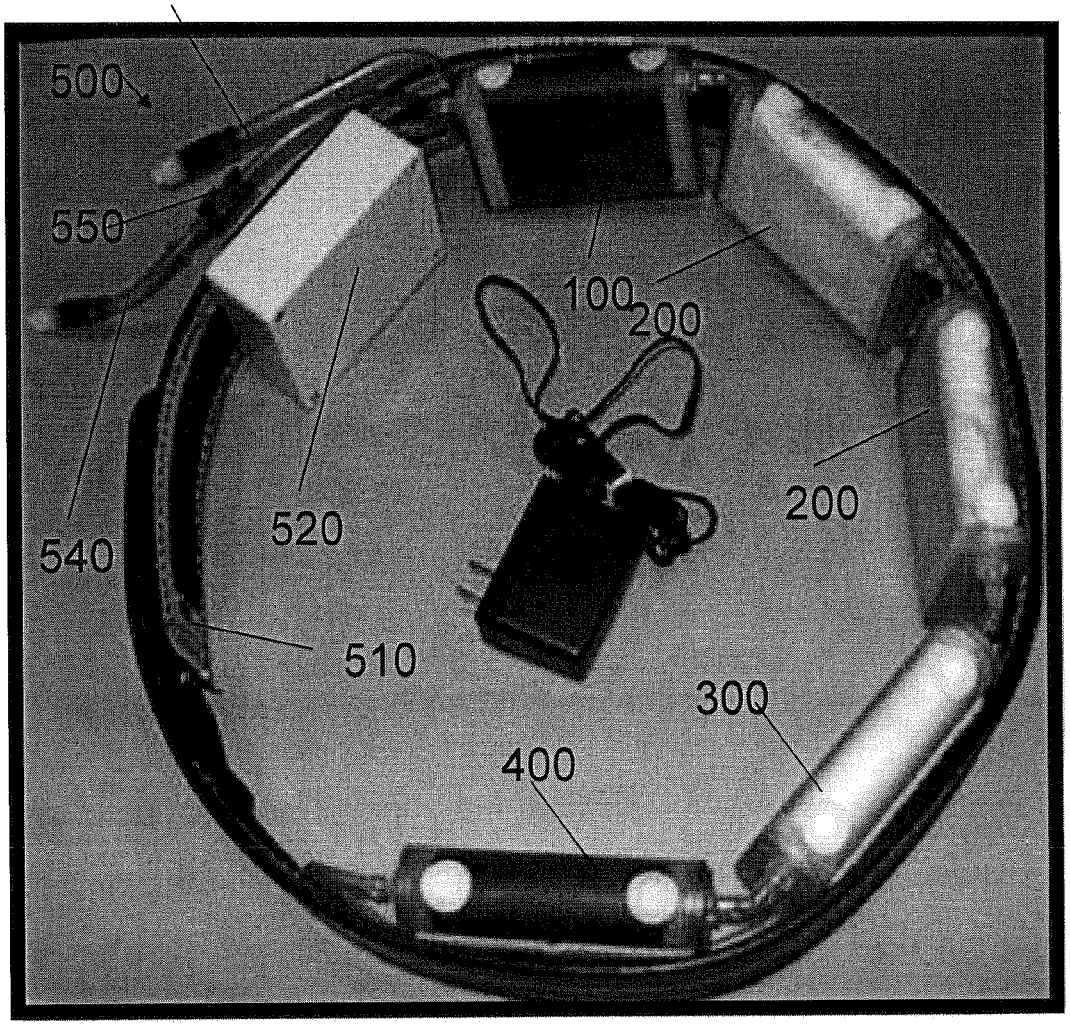
FIG. 20 is a photograph of an embodiment of the portable peritoneal dialysis system in a belt configuration.
Figure 21:
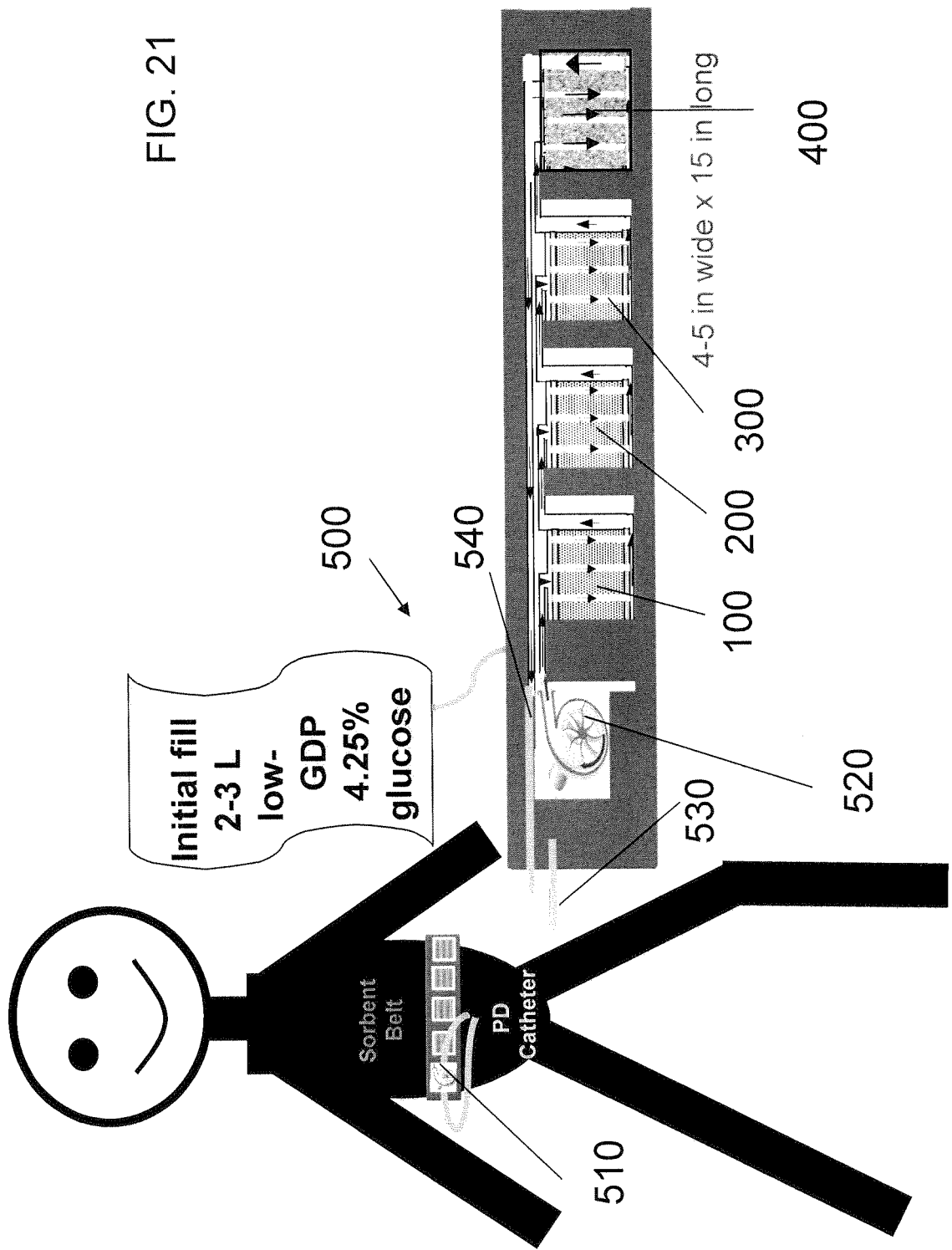
FIG. 21 is a schematic illustration of an embodiment of the portable peritoneal dialysis system in a belt configuration.

Turning now to FIG. 20, in a preferred embodiment, the portable peritoneal dialysis system 500 can be configured as a belt 510. A pump 520 pumps the dialysate through first stage cartridge 100, second stage 200, here shown in the preferred embodiment of two identical cartridges 200, third stage cartridge 300, and fourth stage cartridge 400. The dialysate enters the system through inlet tube 530 and exits the system through outlet tube 540, after passing through the optional ammonia sensor 550. The portable peritoneal dialysis system being worn as a belt is illustrated in FIG. 21.

Figure 22:
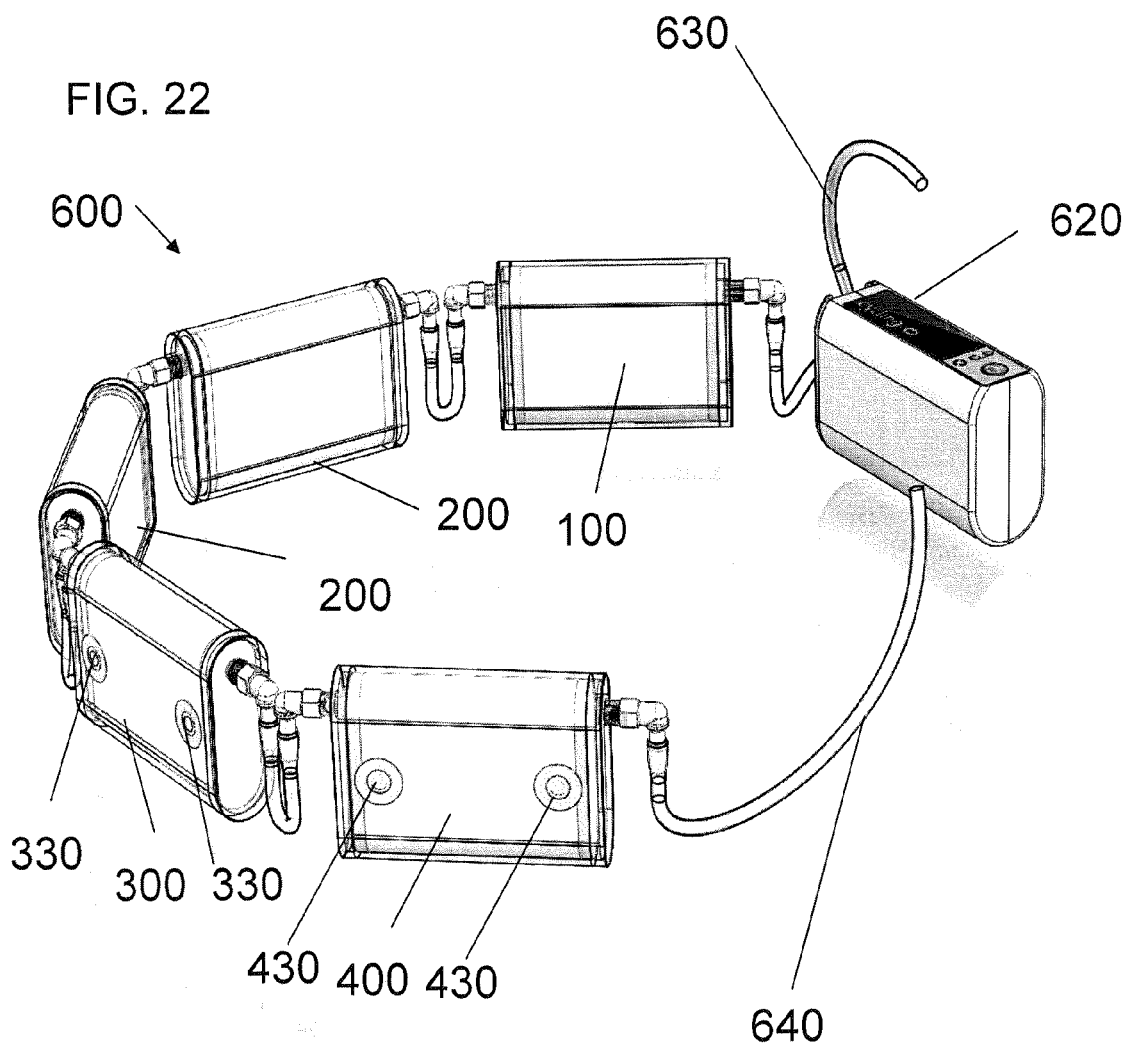
FIG. 22 is an illustration of an embodiment of the portable peritoneal dialysis system in an integrated loop configuration.
Figure 23:
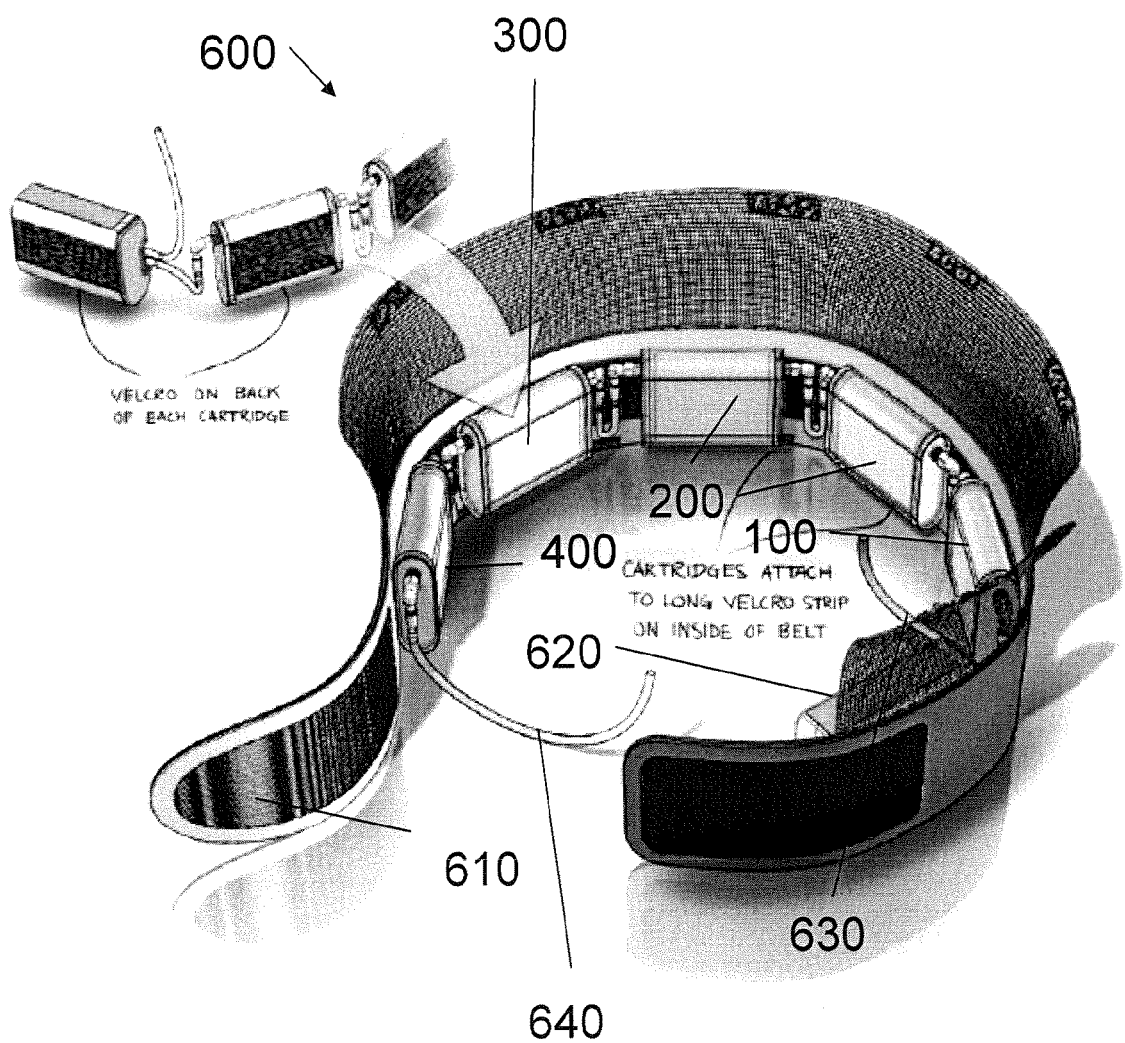
FIG. 23 is an illustration of an embodiment of the integrated loop illustrated in FIG. 22 in a belt configuration.
Figure 24:
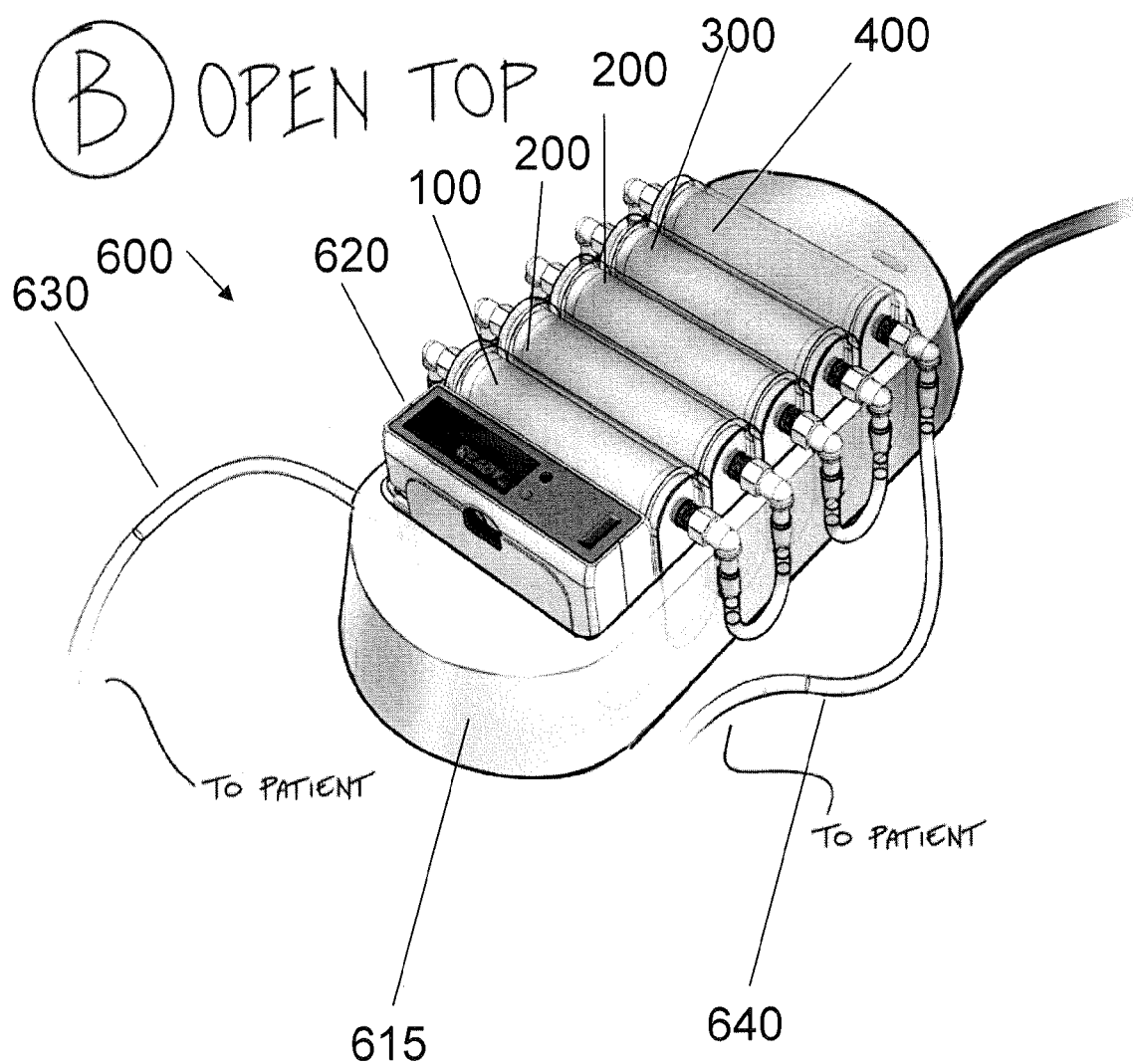
FIG. 24 is an illustration of an embodiment of the integrated loop illustrated in FIG. 22 in a tabletop docking unit configuration.
Figure 25:
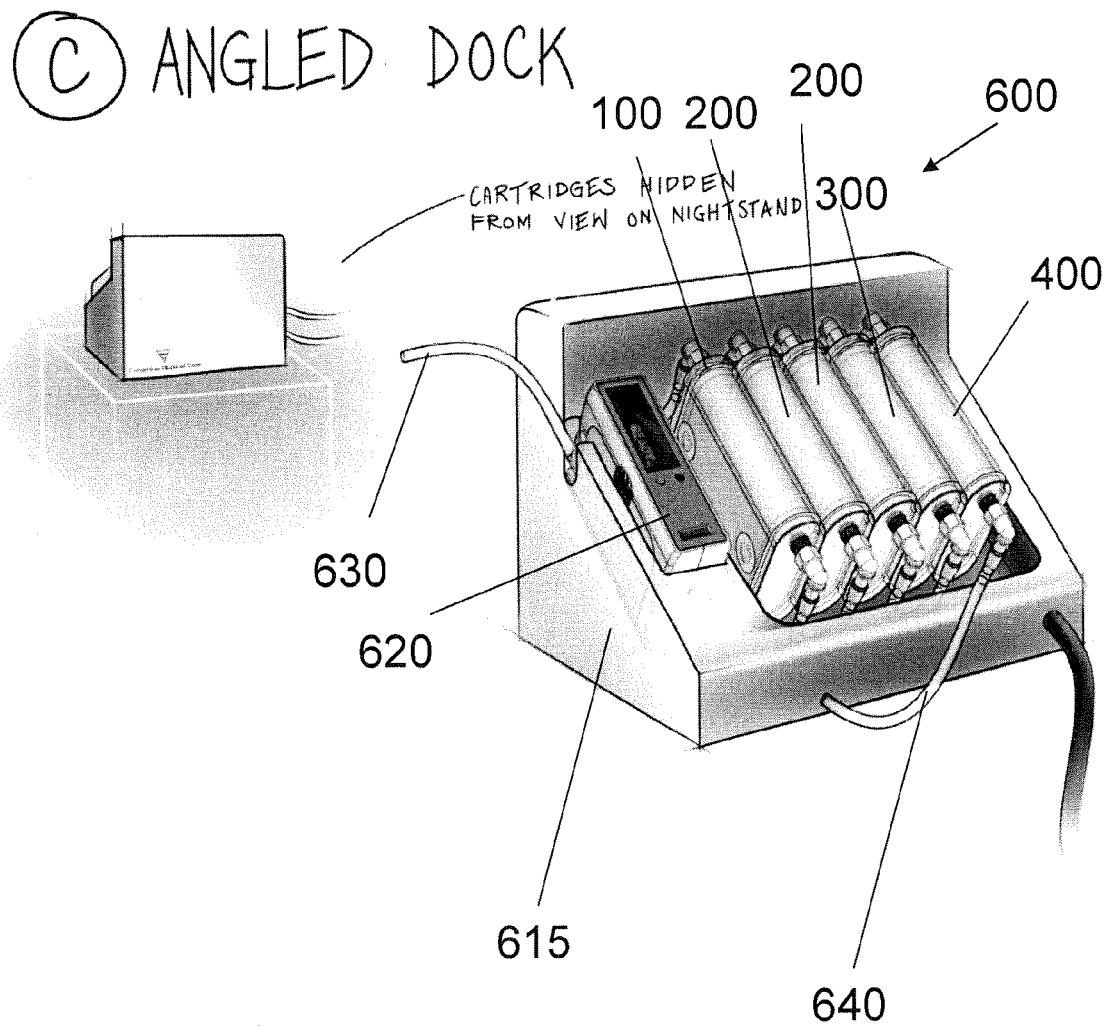
FIG. 25 is an illustration of an embodiment of the integrated loop illustrated in FIG. 22 in an angled tabletop docking unit configuration.

In another embodiment, illustrated in FIG. 22, the peritoneal dialysis system can be configured as an integrated loop. Therein, integrated loop 600 can include a pump 620 that pumps the dialysate through first stage cartridge 100, second stage 200, here shown in the preferred embodiment of two identical cartridges 200, third stage cartridge 300, and fourth stage cartridge 400. The dialysate enters the system through inlet tube 630 and exits the system through outlet tube 640. As illustrated in FIG. 23, the integrated loop can be worn as a belt 610, or alternatively, as illustrated in FIG. 24, the integrated loop can dock into a tabletop docking unit 615. In yet another embodiment, illustrated in FIG. 25, the tabletop docking unit 615 can be arranged with the integrated loop components docked at an angle to the table.

The portable peritoneal dialysis system of this invention can also be configured as a tabletop unit that can be powered by an external power supply, and can also be capable of processing, storing in volatile or non-volatile memory storage, and input/output of patient treatment data (e.g., treatment duration, sensor readings, flow rate, etc.). The tabletop unit can also be linked through a communications network to other computing devices/processes and server computer(s). The communications network can be part of a remote access network, a global network (e.g., the Internet), a worldwide collection of computers, Local area or Wide area networks, and gateways that currently use respective protocols (TCP/IP, Bluetooth, etc.) to communicate with one another.

Figure 26:
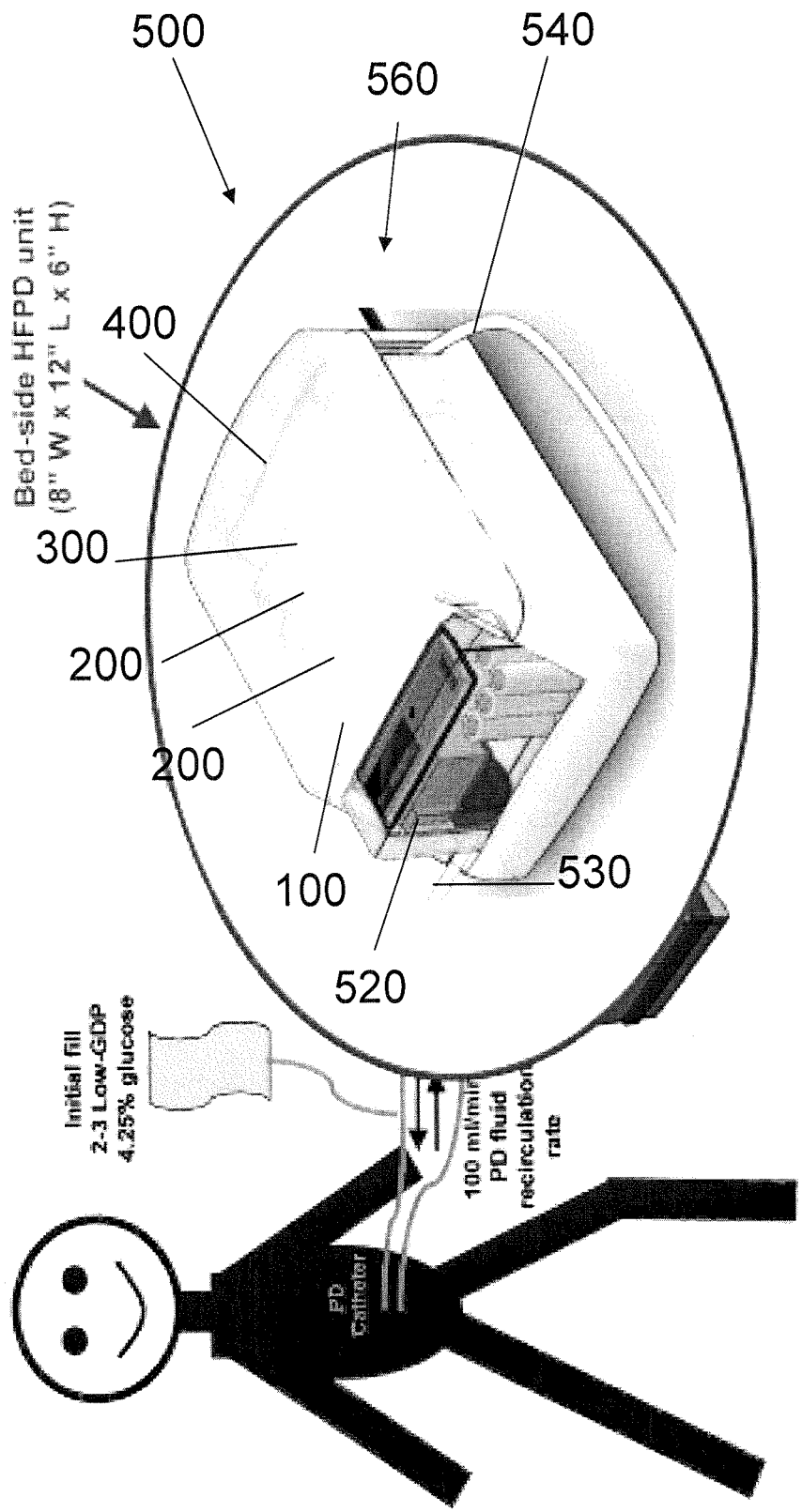
FIG. 26 is an illustration of an embodiment of the portable peritoneal dialysis system in a tabletop configuration.

Turning now to FIG. 26, in one embodiment, the portable peritoneal dialysis system 500 can be configured as a tabletop unit 560. A pump 520 pumps the dialysate through first stage cartridge 100, second stage 200, here shown in the preferred embodiment of two identical cartridges 200, third stage cartridge 300, and fourth stage cartridge 400. The dialysate enters the system through inlet tube 530 and exits the system through outlet tube 540.

The relevant teachings of all patents, published applications and references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims. In particular, the chemical and/or biological experimental data developed in experiments (particularly in animals) or extrapolated therefrom can vary significantly from later developed values appropriate for human beings, as is known by those skilled in the art. Such later-developed values are within the routine skill of practitioners in the art using their own knowledge and the teachings set forth herein.

What is claimed is:

1. A portable peritoneal dialysis system for a patient with renal dysfunction or failure comprising:
    an inlet port for providing inflow to the patient's peritoneal cavity;
    an outlet port for providing outflow from the patient's peritoneal cavity;
    a volume of dialysate for flow into and out of the patient's peritoneal cavity, thereby removing from the patient uremic waste metabolites that have diffused into the dialysate;
    a closed liquid flow loop, including a pump, for flowing the dialysate into and out of the patient's peritoneal cavity;
    an organic-and phosphate-removing stage, including at least one replaceable organic-and phosphate-removing cartridge in the closed liquid flow loop, the cartridge containing a mixture of activated carbon and zirconium oxide packed around semi-permeable hollow fibers for removing organic compounds and phosphate from dialysate removed from the patient's peritoneal cavity; and
    a urea-and ammonia-removing stage, including at least one replaceable urea-and ammonia-removing cartridge separate from the at least one replaceable organic-and phosphate-removing cartridge in the closed liquid flow loop, the at least one replaceable urea- and ammonia-removing cartridge containing material for removing urea and ammonia from dialysate removed from the patient's peritoneal cavity, the material being packed around semi-permeable hollow fibers with interior fiber walls that reject cations, thereby retaining cations in the dialysate.

2. The portable peritoneal dialysis system of claim 1, wherein the material in the cartridge for removing urea and ammonia includes urease and strong acid cation exchange resin or sorbent.

3. The portable peritoneal dialysis system of claim 2, wherein the sorbent includes an ion exchange sorbent.

4. The portable peritoneal dialysis system of claim 2, wherein the urease is in the form of cross-linked jack bean meal polyethylenimine-carbon composite.

5. The portable peritoneal dialysis system of claim 2, further including an ammonia-removing stage, including at least one replaceable cartridge in the closed liquid flow loop, the cartridge containing material for removing ammonia from dialysate removed from the patient's peritoneal cavity, the material being packed around semi-permeable hollow fibers with interior fiber walls that reject cations, thereby retaining cations in the dialysate.

6. The portable peritoneal dialysis system of claim 5, wherein the hollow fibers with interior fiber walls that reject cations reject calcium, magnesium, potassium, and sodium cations.

7. The portable peritoneal dialysis system of claim 1, wherein the material in the cartridge for removing ammonia includes strong acid cation exchange resin or ion exchange sorbent.

8. The portable peritoneal dialysis system of claim 1, further including an organic-and phosphate-removing and pH-control stage, including at least one replaceable cartridge in the closed liquid flow loop, the cartridge containing material for removing organic compounds from dialysate removed from the patient's peritoneal cavity and material for controlling the pH of the dialysate at or near physiological pH.

9. The portable peritoneal dialysis system of claim 8, wherein the material in the cartridge for removing organic compounds includes activated carbon, and the material in the cartridge for controlling the pH of the dialysate includes a mixture of zirconium oxide and sodium zirconium carbonate.

10. The portable peritoneal dialysis system of claim 1, wherein the system is configured as a belt adapted to be worn by the patient.

11. The portable peritoneal dialysis system of claim 1, wherein the system is configured as an integrated loop adapted to be worn by a patient as a belt or docked into a tabletop docking unit.

12. The portable peritoneal dialysis system of claim 1, wherein the system is configured as a tabletop unit.

13. A portable peritoneal dialysis system for a patient comprising:
    an inlet port for providing inflow to the patient's peritoneal cavity;
    an outlet port for providing outflow from the patient's peritoneal cavity;
    a volume of dialysate that is infused into and moved out of the patient's peritoneal cavity, thereby removing from the patient uremic waste metabolites that have diffused into the dialysate;
    a closed liquid flow loop for circulating the dialysate from the patient, throughout the system and back into the patient;
    a pump attached to the closed liquid flow loop for flowing the dialysate into the patient's peritoneal cavity and flowing the dialysate containing uremic waste metabolites out of the patient's peritoneal cavity;
    an organic- and phosphate-removing stage, including at least one replaceable organic- and phosphate-removing cartridge in the closed liquid flow loop, the cartridge containing a mixture of activated carbon and zirconium oxide packed around semi-permeable hollow fibers for removing organic compounds and phosphate from dialysate removed from the patient's peritoneal cavity;
    a urea-and ammonia-removing stage, including at least one replaceable urea-and ammonia-removing cartridge separate from the at least one replaceable organic-and phosphate-removing cartridge in the closed liquid flow loop, the at least one replaceable urea-and ammonia-removing cartridge containing material for removing urea and ammonia from dialysate removed from the patient's peritoneal cavity, the material being packed around semi-permeable hollow fibers with interior fiber walls that reject cations, thereby retaining calcium, magnesium, potassium, and sodium cations in the dialysate;

an ammonia-removing stage, including at least one replaceable cartridge in the closed liquid flow loop, the cartridge comprising material for removing ammonia, the material being packed around semi-permeable hollow fibers with interior fiber walls that reject cations, thereby retaining calcium, potassium, and sodium cations in the dialysate; and an organic-and phosphate-removing and pH-control stage, including at least one replaceable cartridge in the closed liquid flow loop, the cartridge containing material for removing organic compounds and material for controlling the pH of the dialysate at or near physiological pH.

14. A method for providing peritoneal dialysis to a patient using a portable peritoneal dialysis system including a closed liquid flow loop for flowing a volume of dialysate into and out of the patient's peritoneal cavity and through dialysate regenerating stages, comprising:

a) flowing a volume of dialysate from the patient's peritoneal cavity through an organic-and phosphate-removing stage, including at least one replaceable organic- and phosphate-removing cartridge in the closed liquid flow loop, the cartridge containing a mixture of activated carbon and zirconium oxide packed around semi-permeable hollow fibers for removing organic compounds and phosphate from dialysate removed from the patient's peritoneal cavity; thereafter b) flowing the volume of dialysate through semi-permeable hollow fibers contained in a urea-and ammonia-removing stage, including at least one replaceable urea-and ammonia-removing cartridge separate from the at least one replaceable organic-and phosphate-removing cartridge in the closed liquid flow loop, the at least one replaceable urea- and ammonia-removing cartridge containing material for removing urea and ammonia from dialysate removed from the patient's peritoneal cavity, the material being packed around the semi-permeable hollow fibers, the semi-permeable hollow fibers having interior fiber walls that reject cations, thereby retaining cations in the dialysate while removing from the dialysate uremic waste metabolites that have diffused into the dialysate, to produce regenerated dialysate; and c) introducing the regenerated dialysate into the patient's peritoneal cavity.

15. The method for providing peritoneal dialysis to a patient of claim 14, wherein the material in the cartridge for removing urea and ammonia includes urease and strong acid cation exchange resin or sorbent.

16. The method for providing peritoneal dialysis to a patient of claim 15, wherein the sorbent includes an ion exchange sorbent.

17. The method for providing peritoneal dialysis to a patient of claim 15, wherein the urease is in the form of cross-linked jack bean meal polyethylenimine-carbon composite.

18. The method for providing peritoneal dialysis to a patient of claim 15, further including flowing the volume of dialysate through an ammonia-removing stage, including at least one replaceable cartridge in the closed liquid flow loop, the cartridge containing material for removing ammonia from dialysate removed from the patient's peritoneal cavity, the material being packed around semi-permeable hollow fibers with interior fiber walls that reject cations, thereby retaining cations in the dialysate.

19. The method for providing peritoneal dialysis to a patient of claim 18, wherein the hollow fibers with interior fiber walls that reject cations reject calcium, magnesium, potassium, and sodium cations.

20. The method for providing peritoneal dialysis to a patient of claim 14, wherein the material in the cartridge for removing ammonia includes strong acid cation exchange resin or ion exchange sorbent.

21. The method for providing peritoneal dialysis to a patient of claim 14, further including flowing the volume of dialysate through an organic- and phosphate-removing and pH-control stage, including at least one replaceable cartridge in the closed liquid flow loop, the cartridge containing material for removing organic compounds from dialysate removed from the patient's peritoneal cavity and material for controlling the pH of the dialysate at or near physiological pH.

22. The method for providing peritoneal dialysis to a patient of claim 21, wherein the material in the cartridge for removing organic compounds includes activated carbon, and the material in the cartridge for controlling the pH of the dialysate includes a mixture of zirconium oxide and sodium zirconium carbonate.

23. The method for providing peritoneal dialysis to a patient of claim 14, wherein the system is configured as a belt adapted to be worn by the patient.

24. The method for providing peritoneal dialysis to a patient of claim 14, wherein the system is configured as an integrated loop adapted to be worn by a patient as a belt or docked into a tabletop docking unit.

25. The method for providing peritoneal dialysis to a patient of claim 14, wherein the system is configured as a tabletop unit.

* * * * *